(12) United States Patent
Ji et al.

(10) Patent No.: US 9,631,196 B2
(45) Date of Patent: Apr. 25, 2017

(54) GENETIC MANIPULATION AND EXPRESSION SYSTEMS FOR PUCCINIOMYCOTINA AND USTILAGINOMYCOTINA SUBPHYLA

(75) Inventors: Liang Hui Ji, Singapore (SG); Yan Bin Liu, Singapore (SG); John Chong Mei Koh, Singapore (SG); Long Hua Sun, Singapore (SG)

(73) Assignee: TEMASEK LIFE SCIENCES LABORATORY LIMITED, Singapore (SG)

( * ) Notice: Subject to any disclaimer, the term of this patent is extended or adjusted under 35 U.S.C. 154(b) by 21 days.

(21) Appl. No.: 14/124,447

(22) PCT Filed: May 10, 2012

(86) PCT No.: PCT/SG2012/000164
§ 371 (c)(1),
(2), (4) Date: Dec. 6, 2013

(87) PCT Pub. No.: WO2012/169969
PCT Pub. Date: Dec. 13, 2012

(65) Prior Publication Data
US 2014/0113377 A1    Apr. 24, 2014

Related U.S. Application Data

(60) Provisional application No. 61/495,619, filed on Jun. 10, 2011.

(51) Int. Cl.
| | | |
|---|---|---|
| *A61K 39/00* | (2006.01) | |
| *C07H 21/02* | (2006.01) | |
| *C07H 21/04* | (2006.01) | |
| *C12N 15/80* | (2006.01) | |
| *C07K 14/38* | (2006.01) | |
| *C12N 15/10* | (2006.01) | |

(52) U.S. Cl.
CPC .............. *C12N 15/80* (2013.01); *C07K 14/38* (2013.01); *C12N 15/1086* (2013.01)

(58) Field of Classification Search
CPC ................................ C12R 1/6455; C12N 1/14
See application file for complete search history.

(56) References Cited

FOREIGN PATENT DOCUMENTS

| CA | 2334215 A1 | 12/1999 |
|---|---|---|
| WO | 9964587 A1 | 12/1999 |
| WO | 02053728 A2 | 7/2002 |
| WO | 2011/053612 A1 | 5/2011 |
| WO | 2011053612 A1 | 5/2011 |

OTHER PUBLICATIONS

Ji, L. et al. Fungal Genetrics and Biology. vol. 47, pp. 279-287, Jan. 15, 2010.*
Cheng, Y. L. et al., "Establishment of a gene transfer system from Pseudozyma flocculosa, an antagonistic fungus of powdery mildew fungi," Mol. Genet Genomics, 2001, 286:96-102.
Goldstein, A., et al., "Three new dominant drug resistance cassettes for gene disruption in *Saccharomyces cerevisiae*," Yeast, 1999, 15:1541-1553.
Smith, T. L., et al., "Isolation and characterization of a Ustilago maydis glyceraldehyde-3-phosphate dehydrogenase-encoding gene," Gene, 1990, 93(1):111-117.
Written Opinion issued for Singapore patent application No. 2013089891 dated Feb. 10, 2015, 20 pages.
Kojic, et al., "Shuttle vectors for genetic manipulations in Ustilago maydis," Can. J. Microbiol., 46:333-338, 2000.
Search report in corresonding European Application No. 12796180.3 dated Dec. 22, 2014, 6 pages.
Ji, Lianghui et al., "A Simplified and Efficient Method for Transformation and Gene Tagging of Ustilago maydis Using Frozen Cells," Fungal Genetics and Biology, 2010, vol. 47, pp. 279-287, copyright 2010 Elsevier Inc.
GenBank Accession No. X07879.1, "Ustilaga maydis Gene for Glyceraldehyde-3-Phosphate Dehydrogenase (gapd, EC 1.2.1.12.)," Nov. 14, 2006, 2 pages.
Avis, Tyler J. et al., "Usefulness of Heterologous Promoters in the Pseudozyma Flocculosa Gene Expression System," Bioscience, Biotechnology and Biochemistry, 2008, vol. 72, No. 2, pp. 456-462.
Liu, Y. et al., "Characterization of Glyceraldehyde-3-Phosphate Dehydrogenase Gene RtGPD1 and Development of Genetic Transformation Method by Dominant Selection in Oleaginous Yeast Rhodosporidium toruloides," Applied Microbiology and Biotechnology, Jun. 22, 2012, pp. 1-11, copyright Springer-Verlag 2012.
GenBank Accession No. JF412803.1, "Synthetic Construct Hygromycin B Phosphotransferase (hpt-2) Gene, complete cds," Jul. 2, 2011, 1 page.
Singapore Search Report and Written Opinion, issued for Singapore Application No. 2013089891, mailed Jan. 30, 2015, 18 pages.
Ji, L. et al., "A simplified and efficient method for transformation and gene tagging of Ustilago maydis using frozen cells," Fungal Genetics and Biology, 47 (2010) 279-287.
First Office Action issued in related pending Chinese patent application No. 201280038496.0 mailed Nov. 20, 2015, with English translation, 13 pages.
GenBank: X07879.1, Ustilaga maydis gene for glyceraldehyde-3-phosphate dehydrogenase (gapd, EC 1.2.1.12.), Retrieved from http://www.ncbi.nlm.nih.gov/nuccore/X07879, 2 pages.
Office Action No. 1 issued in related Australian patent application No. 2012267241 dated Jun. 3, 2016, 4 pages.

* cited by examiner

*Primary Examiner* — Rodney P Swartz
(74) *Attorney, Agent, or Firm* — Rothwell, Figg, Ernst & Manbeck, P.C.

(57) ABSTRACT

The present invention relates to the application of isolated promoters and synthetic dominant selection constructs and enhancers for gene targeting for efficient production of genetically modified cells in a species selected from the Pucciniomycotina and Ustilaginomycotina subphyla, in particular, species selected from the *Rhodosporidium, Sporisorium, Sporobolomyces* or *Ustilago* genera.

17 Claims, 7 Drawing Sheets

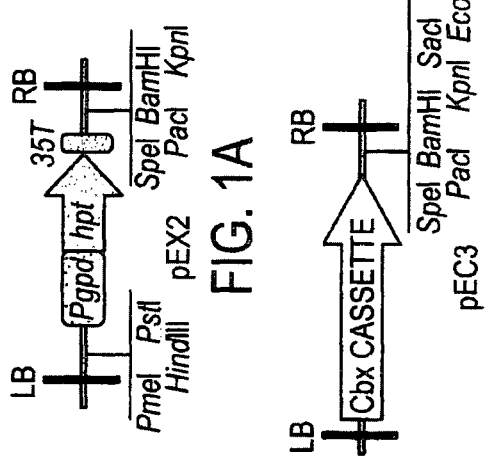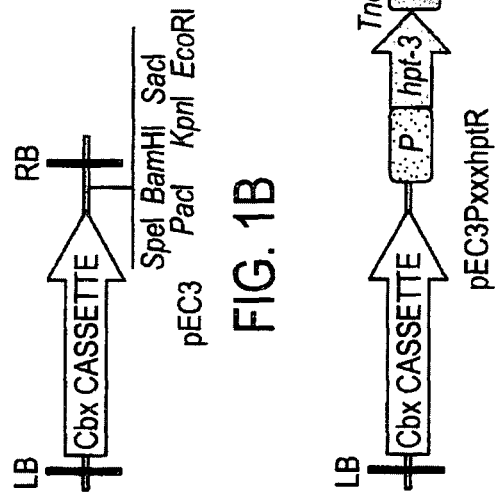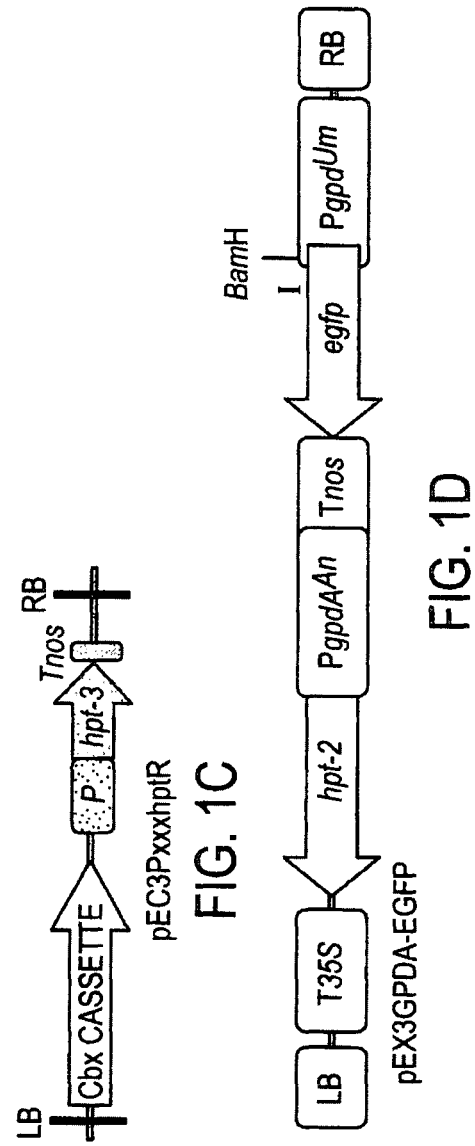
FIG. 1A
FIG. 1B
FIG. 1C
FIG. 1D 2-(4-MORPHOLINYL)-4H-NAPHTHOL[1,2-b]PYRAN-4-ONE

GENETIC MANIPULATION AND EXPRESSION SYSTEMS FOR PUCCINIOMYCOTINA AND USTILAGINOMYCOTINA SUBPHYLA

CROSS-REFERENCE TO RELATED APPLICATION

The present application is a national phase entry under 35 U.S.C. §371 of PCT/SG2012/000164, filed 10 May 2012, which is related to and claims priority to U.S. provisional patent application Ser. No. 61/495,619, filed 10 Jun. 2011. Each application is incorporated herein by reference in its entirety.

SEQUENCE SUBMISSION

The present application is being filed along with a Sequence Listing in electronic format. The Sequence Listing is entitled 2577207SequenceListing.txt, was created on 11 Apr. 2012 and is 31 kb in size. The information in the electronic format of the Sequence Listing is part of the present application and is incorporated herein by reference in its entirety.

BACKGROUND OF THE INVENTION

The present invention relates to the field of plant molecular biology, more particularly to high efficiency genetic manipulation and strong gene expression systems in species in the Pucciniomycotina and Ustilaginomycotina subphyla.

The publications and other materials used herein to illuminate the background of the invention, and in particular, cases to provide additional details respecting the practice, are incorporated by reference, and for convenience are referenced in the following text by author and date and are listed alphabetically by author in the appended bibliography.

The Pucciniomycotina are a subphylum of fungi in the phylum of Basidiomycota (Kirk et al., 2008). It holds many species that have important industrial applications. For example, a number of species in the Rhodosporidium and Sporidiobolus genera, such as Rhodosporidium toruloides (also known as Rhodotorula gracilis, Rhodosporidium glutinis, Rhodotorula glutinis, Torula koishikawensis and Torula rubescens) and Sporobolomyces salmonicolor, are oil-rich single-cell yeasts capable of high density fermentation (Hu et al., 2009; Meng et al., 2009). These species hold great potential as a host for the production of long chain hydrocarbons, such as triacylglycerol (TAG, or fat), fatty acid esters (biodiesel), fatty alcohols, alcohols, lactones, terpenoids and vitamins (Wu et al., 2010a; Wu et al., 2010b; Zhao et al., 2010a; Zhao et al., 2010b). Although a method based on the PEG-mediated transfection of protoplast have been reported in Rhodosporidium toruloides (Tully and Gilbert, 1985), the method is highly unreliable and requires an auxotrophic mutant for transformation. The transformation vector cannot be applied to genetic manipulation of industrials strains due the instability of the plasmid pHG2, which contains the Phenylalanine Ammonia-lyase (PAL)-coding gene (PAL) of R. toruloides and LEU2 gene of Saccharomyces cerevisiae as a selection marker, and the site-specific pattern of DNA vector integration. Similarly, there are no functional promoters that can be used to drive the expression of utility genes or selections markers in Rhodosporidium. Similar situation is found in Sporobolomyces (Ianiri et al., 2011). In another example, species in Ustilaginomycotina subphylum, in particular, Ustilago and Pseudozyma genera, are known to produce glycolipids, which may function as a surfactant or fungicide (Hewald et al., 2005; Teichmann et al., 2010).

A complete genetic manipulation and expression system is typically composed of promoters that are either constitutive or inducible; selection markers; DNA vectors; methods to introduce the DNA into the host cell, either to integrate into the genome or replicate as an episome; and methods to inhibit or block expression of genes of interest.

Agrobacterium tumefaciens-mediated transformation (ATMT) is a convenient method for transformation of many fungal species (De Groot et al., 1998). Transformation efficiency may be improved by optimization of pH value for the Agrobacterium, ratio and absolute value of recipient cells and donor cells during co-culture (Ji et al., 2010) and the use of enhancer DNA sequences derived from T-DNA (YE and Gilbertson, 2009). In ATMT of plant species several techniques have been reported to improve transformation, including sonication and vacuum infiltration of plant tissues (de Oliveira et al., 2009); stronger promoters to drive expression of selection markers (Maehara et al., 2010) and control of host defense response (Khanna et al., 2007; Vega et al., 2008). The effects of these modifications have not been confirmed in the ATMT of fungi.

It is well-known that fungal cells may also be transformed by electroporation of either intact cells or protoplast (Wu and Letchworth, 2004); and transfection of a protoplast (Meyer, 2008; Turgeon et al., 2010) or simple chemical induction to increase cell wall permeability (Gietz and Woods, 2002; Hill et al., 1991; Ito et al., 1983). Random insertional mutagenesis is a powerful tool for fast identification of unknown genes. Although restriction enzyme-mediated integration (REMI) may be used to improve integration of linearized DNA vectors in a PEG-mediated transformation protocol (Bölker et al., 1995; Maier and Schafer, 1999), this method is hampered by large deletions of genomic DNA, multiple insertions and untagged mutagenesis including chromosomal rearrangements (Bölker et al., 1995; Meyer et al., 2003; Sweigard et al., 1998). On the other hand, ATMT has been recognized as a superior tool on this aspect (Choi et al., 2007; Soltani et al., 2008).

Selection of fungal transformants has been demonstrated with artificial constructs that express a protein that modifies the antibiotic or herbicide. Commonly used genes include hygromycin phosphotransferase (hpt) that confers resistance to Hygromycin B (Bundock et al., 1995); nourseothricin acetyltransferase (nat) that confers resistance to Nourseothricin (Ji et al., 2010; Krugel et al., 1988), aminoglycoside 3'-phosphotransferase (aph) or Neomycin phosphotransferase (npt) that confers resistance to Kanamycin or G418 or Neomycin (Goldstein and McCusker, 1999; Scorer et al., 1994), Streptoalloteichus hindustanus bleomycin gene (ble) that confers resistance to Zeocin (Pfeifer et al., 1997; Takeno et al., 2005); 5-enolpyruvyl-3-phosphoshikimate synthetase (aroA) gene confers resistance to the herbicide Glyphosate (Comai et al., 1983); phosphinothricin acetyl transferase (pat) that confers resistance to the herbicide bialaphos (Goldstein and McCusker, 1999); acetolactate synthase (acs) gene that confers resistance to the herbicide Sulfonylureas (Haughn et al., 1988).

Gene deletion and replacement are vital gene-targeting techniques in modern genetics. However, it is often very challenging to generate such mutants due to the low gene-targeting frequency. Techniques that significantly improve gene-targeting frequency are highly sought after in many organisms.

In higher eukaryotic DNA nonhomologous end joining (NHEJ) system, the DNA-dependent protein kinase (DNA-PK) holoenzyme comprises a polypeptide heterodimer of approximately 70 and 80 kDa, known as Ku70 and Ku80, which binds to DNA strand breaks, thereby recruiting and activating the 470-kDa catalytic subunit, termed as DNA-PKcs (Smith and Jackson, 1999). Whilst Rad51 and Rad52 are essential for the repair of DSB in the HR pathway (van Attikum et al., 2003), DNA-PKcs/Ku complex and XRCC4/ligase IV are vital in the NHEJ pathway in mammalian systems (van Attikum et al., 2001). However, homolog for the DNA-PKcs subunit remains unidentified in fungi. In recent years, there have been several reports of success on improvement of gene deletion frequency through disruption of the NHEJ pathway by deleting one or more of its key components (Kück and Hoff, 2010). This technique is cumbersome to apply.

On the other hand, a large number of compounds have been reported to inhibit the activity of DNA-PK, including wortmanin (Boulton et al., 1996), LY294002 (Rosenzweig et al., 1997), vanillin (Durant and Karran, 2003), NU1025 (Boulton et al., 1999), PD128763 (Tentori et al., 2002), AG14361 (Skalitzky et al., 2003), NU7026 [2-(morpholin-4-yl)-benzo[h]chomen-4-one; 2-(4-morpholinyl)-4H-naphthol[1,2-b]pyran-4-one] and NU7441 [8-(4-dibenzothienyl)-2-(4-morpholinyl)-4H-1-benzopyran-4-one]. The latter two are believed to be more specific and potent inhibitors of DNA-PK in animals (Veuger et al., 2003; Willmore et al., 2004). In the absence of DNA-PK in fungi, it is not known if there compounds will facilitate gene targeting.

Currently, genetic transformation of species in the *Rhodosporidium, Sporobolomyces, Sporisorium* and *Ustilago* genera is either completely not available or inefficient, and is a major hurdle to the advancement of renewable chemicals and biofuels.

SUMMARY OF THE INVENTION

The present invention relates to synthetic constructs and the transformation methods that enable highly efficient production of a transformed cell selected from a species in the Pucciniomycotina and Ustilaginomycotina subphyla. The species of particular relevance are those in the *Rhodosporidium, Sporisorium, Sporobolomyces* and *Ustilago* genera, in which reside a number of species with great potential for the bioconversion of renewable resources into high-value products, such as triglyceride, biodiesel, fatty alcohol, vitamins, lactone, terpenoids and biosurfactants.

In a first aspect, the present invention provides polynucleotide sequences that function as a strong promoter of gene expression, for example, for the hygromycin phosphotransferase (hpt) and nourseothricin acetyltransferase genes (nat), and allows the effective selection of transformed cells in species selected from the *Rhosporidium, Sporisorium* and *Ustilago* genera. In one embodiment, the promoter comprises the nucleotide sequence set forth in SEQ ID NO:1. In another embodiment, the promoter comprises the nucleotide sequence set forth in SEQ ID NO:2. In an additional embodiment, the promoter comprises the nucleotide sequence set forth in SEQ ID NO:3. In a further embodiment, the promoter comprises the nucleotide sequence set forth in SEQ ID NO:4. In another embodiment, the promoter is a tef promoter of *Ashibia gossipii* and comprises the nucleotide sequence set forth in SEQ ID NO: 5. In an additional embodiment, the promoter comprises the nucleotide sequence set forth in SEQ ID NO:51. In a further embodiment, the promoter comprises the nucleotide sequence set forth in SEQ ID NO:55. In another embodiment, the promoter is a stearoyl-CoA delta9-desaturase promoter of *Rhodotrula glutinis* and comprises the nucleotide sequence set forth in SEQ ID NO:56. Each of these promoters are effective in performing strong gene expression in *Rhosporidium, Sporisorium, Sporobolomyces, Rhodoturula, Pseudozyma* and *Ustilago* genera. Additional strong promoters can be identified from other species in the *Aspergillus, Rhosporidium, Rhodotorula, Sporobolomyces, Sporisorium, Pseudozyma* and *Ustilago* genera using the techniques described herein for identifying such promoters. In addition, operable fragments of these promoters can be isolated using convention promoter screening assays and can be screened for efficient selection of transformed fungal cells using the techniques described herein.

In a second aspect, the present invention provides synthetic dominant selection constructs comprising an isolated promoter derived from a species selected from the *Aspergillus, Rhosporidium, Sporobolomyces, Sporisorium, Rhodoturula, Pseudozyma* and *Ustilago* genera, to which the promoter is operatively linked to a coding sequence for a suitable marker which is operatively linked to a transcriptional terminator. Such constructs are effective in facilitating production of a transformed cell in a species selected from the *Rhosporidium, Sporisorium, Sporobolomyces, Rhodoturula, Pseudozyma* or *Ustilago* genus. In one embodiment, a suitable marker is a protein that confers antibiotic resistance. In another embodiment, a suitable marker is a protein that confers herbicide resistance. In one embodiment, a coding sequence for the marker that fulfills this function is one that is either naturally existent or artificially created and contains at least about 60% GC. In a second embodiment, a coding sequence for the marker that fulfills this function is one that is either naturally existent or artificially created and contains about 63% GC. In a third embodiment, a coding sequence for the marker that fulfills this function is one that is either naturally existent or artificially created and contains about 70% GC. In one embodiment, at least about 70% of the codon triplets of such coding sequences end with C or G. In another embodiment, more than about 80% of the codon triplets of such coding sequences end with C or G. In one embodiment, such coding sequences are composed of UCG codons in at least about 40% of the total Serine (Ser) residues. In one embodiment, the coding sequence for drug resistance comprises the nucleotide sequence set forth in SEQ ID NO:6. In another embodiment, the coding sequence for drug resistance comprises the nucleotide sequence set forth in SEQ ID NO:7. In an additional embodiment, the coding sequence for drug resistance comprises the nucleotide sequence set forth in SEQ ID NO:8. In one embodiment, any transcriptional terminator operable in a fungal species can be used.

In a third aspect, the present invention provides a transformation method that is based on dominant selection for a species selected from Pucciniomycotina and Ustilaginomycotina subphyla, in particular, a species in the *Rhosporidium, Sporisorium, Ustilago, Rhodoturula, Pseudozyma* or *Sporobolomyces (Sporidiobolus)* genus. In one embodiment, the transformation method is *Agrobacterium tumefaciens*-mediated transformation (ATMT). In another embodiment, the transformation method is electroporation. In an additional embodiment, the transformation method is transfection. In a further embodiment, the transformation method is biolistic.

According to the ATMT embodiment, the method comprises the steps: (a) creating a synthetic DNA construct that comprises (i) a promoter derived from the *Aspergillus,*

Rhosporidium, Sporobolomyces, Sporisorium, Rhodoturula, Pseudozyma or Ustilago genera operatively linked to (ii) a coding sequence for a selectable marker operatively linked to (iii) a transcriptional terminator that are operatively linked; (b) inserting the DNA construct into a T-DNA binary vector; (c) introducing the resulting T-DNA vector into a strain of Agrobacterium; (d) co-culturing the Agrobacterium cells with fungal cells on a solid medium, or on a membrane that is laid on top of a solid medium, preferably in the presence of Agrobacterium virulence inducer, such as acetosynringone (AS) to transform fungal cells; (e) selecting a transformed colony directly on a solid medium or on a membrane that is laid atop of a solid medium. The selection medium can be further supplemented with agents at a concentration that completely suppress the growth of Agrobacterium and non-transformed fungal cells. In one embodiment, the promoter is one described herein. In another embodiment, the coding sequence for a selectable marker is one described herein. In one embodiment, the selection or co-culturing media contains at least about 1.5% agar. In another embodiment, the selection or co-culturing media contains between about 2% and about 3% agar.

In a fourth aspect, the present invention provides an improved method for gene targeting in fungi. In particular, a mammalian DNA-dependent protein kinase (DNA-PK) inhibitor can be supplemented at a substantial amount to a medium used for transformation. In one embodiment, the DNA-PK inhibitor is NU7026 (2-(morpholin-4-yl)-benzo[h]chomen-4-one; 2-(4-morpholinyl)-4H-naphthol[1,2-b] pyran-4-one). In another embodiment, the amount of NU7026 in the medium is between about 0.1 µM and about 50 µM. In an additional embodiment, the DNA-PK inhibitor can be used with any transformation protocol, such as ATMT, electroporation, transfection, biolistic and the like.

BRIEF DESCRIPTION OF THE FIGURES

FIGS. 1A-1D show illustrations of transformation vectors. FIG. 1A: pEX2; Pgpd refers to gpd promoter of Ustilago maydis. FIG. 1B: pEC3. FIG. 1C: pEC3PxxxhptR; Pxxx indicates various promoters located in the P box. FIG. 1D: pEX3GPDA-EGFP. LB and RB are the left border and right border of T-DNA respectively. T35S: Cauliflower mosaic 35S gene terminator; Tnos: Agrobacterium tumefaciens nopaline synthase transcriptioanl termiantor; egfp: Enhanced Green Florescence Protein gene.

FIG. 2A: R. toruloides co-cultured with AGL1. FIG. 2B: R. toruloides co-cultured with AGL1 (pEX2). FIG. 2C: colony PCR of putative transformants. FIG. 2D: colony PCR of putative transformants using nat as a selection marker.

FIG. 3A: Colonies selected for 8 days against 100 µg/ml hygromycin B; FIG. 3B: Colonies selected for 8 days against 200 µg/ml hygromycin B.

DETAILED DESCRIPTION OF THE INVENTION

Figure 2C:
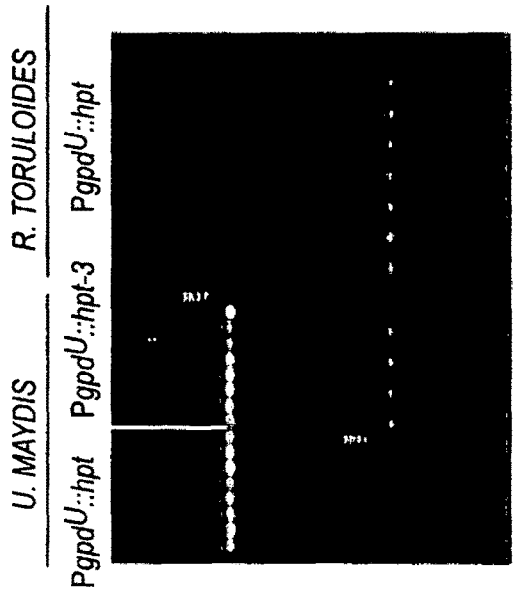
FIGS. 2A-2D show the effect of selection markers on ATMT of R. toruloides. Selection for transformants was performed with 100 µg/ml Hygromycin B for both U. maydis and R. toruloides.

Unless defined otherwise, all technical and scientific terms used herein have the same meaning as is commonly understood by one of skill in the art to which the invention belongs.

The term "efficient selection" as used herein means direct selection for at least two true transformants in a 90 mm Petri dish using any fungal isolates.

The term "strong expression" as used herein means expression of a marker protein or mRNA to a detectable level using detection methods known, for example, florescence for GFP, activity assay for GUS and lacZ genes.

The present invention relates to synthetic constructs and transformation methods that enable highly efficient production of a transformed cell selected from a species Pucciniomycotina and Ustilaginomycotina subphyla. The species of particular relevance are those in the Rhodosporidium, Sporobolomyces, Sporisorium, Rhodoturula, Pseudozyma and Ustilago genera, in which reside a number of species with great potential for the bioconversion of renewable resources into high-value products, such as triglycerides, biodiesel, fatty alcohol, lactone, terpendoid and vitamins and biosurfactants. Examples of such strains include, but are not limited to, Rhodosporidium toruloides, Rhodosporidium azoricum, Rhodosporidium babjevae, Rhodosporidium concentricum, Rhodosporidium diobovatum, Rhodosporidium fluvial, Rhodosporidium kratochvilovae, Rhodosporidium lusitaniae, Rhodosporidium paludigenum, Rhodosporidium sphaerocarpum, Rhodosporidium toruloides, Sporobolomyces roseus, Sporobolomyces carnicolor, Sporobolomyces salmoneus, Sporisorium scitamineum, Ustilago maydis, Pseudozyma Antarctica, Pseudozyma aphidis.

In one aspect, the present invention provides a polynucleotide construct comprising a promoter operatively linked to a coding sequence for a selectable marker operatively linked to a transcriptional terminator. The promoter is derived from a fungal species selected from the group of a species of the Ustilago genus, a species of the Aspergillus genus and a species of the Rhodosporidium genus and provides for the strong expression of the coding sequence in transformed fungal cell of the Pucciniomycotina and Ustilaginomycotina subphyla. The polynucleotide construct provides efficient selection of a transformed fungal cells of the Pucciniomycotina and Ustilaginomycotina subphyla. The polynucleotide construct is particularly useful for efficient selection of transformed fungal cells of the Rhodosporidium, Sporisorium, Ustilago, Rhodoturula, Pseudozyma and Sporobolomyces (Sporidiobolus) genera.

In one embodiment the promoter is derived from a gene encoding glyceraldehyde 3-phosphate dehydrogenase (gpd) or from a gene encoding protein translation elongation factor (tef).

In one embodiment, the promoter comprises the nucleotide sequence set forth in SEQ ID NO:1. In another embodiment, the promoter comprises the nucleotide sequence set forth in SEQ ID NO:2. In an additional embodiment, the promoter comprises the nucleotide sequence set forth in SEQ ID NO:3. In a further embodiment, the promoter comprises the nucleotide sequence set forth in SEQ ID NO:4. In another embodiment, the promoter is the tef promoter of *Ashibia gossipii* set forth in SEQ ID NO: 5. In an additional embodiment, the promoter comprises the nucleotide sequence set forth in SEQ ID NO:51. In a further embodiment, the promoter comprises the nucleotide sequence set forth in SEQ ID NO:55. In another embodiment, the promoter is a stearoyl-CoA delta9-desaturase promoter of *Rhodotrula glutinis* and comprises the nucleotide sequence set forth in SEQ ID NO:56. Additional strong promoters can be identified from other species in the *Aspergillus, Rhosporidium, Rhodotorula, Sporobolomyces* and *Ustilago* genera using the techniques described herein for identifying such promoters. In addition, operable fragments of these promoters can be isolated using convention promoter screening assays and can be screened for efficient selection of transformed fungal cells using the techniques described herein.

Nucleic acid hybridization, a technique well known to those of skill in the art of DNA manipulation, can be used to identify other suitable polynucleotides. In accordance with the invention other suitable promoters for use may be obtained by the identification of polynucleotides that selectively hybridize to the promoters described above by hybridization under low stringency conditions, moderate stringency conditions, or high stringency conditions. Selectively hybridizing sequences typically have at least 50% sequence identity, preferably at least 70%, 80% or 90% sequence identity, and most preferably 95%, 98% or 99% sequence identity with each other.

Database searches and homology searches of genome and nucleotide databases identify similar DNA or RNA molecules based on the alignment of nucleotides using algorithms or computer programs and these techniques well known to those of skill in the art. In accordance with the invention other suitable polynucleotides for use may be obtained by the in silico identification of polynucleotides for regulatory sequences with at least 50% sequence identity, preferably at least 70%, 80% or 90% sequence identity, and most preferably 95%, 98% or 99% sequence identity with each other.

In one embodiment, the promoter comprises (i) a nucleotide sequence having at least 50% identity with the nucleotide sequence of SEQ ID NO:2, (ii) a promoter comprising a nucleotide sequence having at least 60% identity with the nucleotide sequence of SEQ ID NO:2, (iii) a promoter comprising a nucleotide sequence having at least 70% identity with the nucleotide sequence of SEQ ID NO:2, (iv) a promoter comprising a nucleotide sequence having at least 80% identity with the nucleotide sequence of SEQ ID NO:2, (v) a promoter comprising a nucleotide sequence having at least 90% identity with the nucleotide sequence of SEQ ID NO:2, (vi) a promoter comprising a nucleotide sequence having at least 95% identity with the nucleotide sequence of SEQ ID NO:2, and (vii) a promoter comprising a nucleotide sequence having at least 98% identity with the nucleotide sequence of SEQ ID NO:2.

In another embodiment, the promoter comprises (i) a nucleotide sequence having at least 50% identity with the nucleotide sequence of SEQ ID NO:51, (ii) a promoter comprising a nucleotide sequence having at least 60% identity with the nucleotide sequence of SEQ ID NO:51, (iii) a promoter comprising a nucleotide sequence having at least 70% identity with the nucleotide sequence of SEQ ID NO:51, (iv) a promoter comprising a nucleotide sequence having at least 80% identity with the nucleotide sequence of SEQ ID NO:51, (v) a promoter comprising a nucleotide sequence having at least 90% identity with the nucleotide sequence of SEQ ID NO:51, (vi) a promoter comprising a nucleotide sequence having at least 95% identity with the nucleotide sequence of SEQ ID NO:51, and (vii) a promoter comprising a nucleotide sequence having at least 98% identity with the nucleotide sequence of SEQ ID NO:51.

In a further embodiment, the promoter comprises (i) a nucleotide sequence having at least 50% identity with the nucleotide sequence of SEQ ID NO:55, (ii) a promoter comprising a nucleotide sequence having at least 60% identity with the nucleotide sequence of SEQ ID NO:55, (iii) a promoter comprising a nucleotide sequence having at least 70% identity with the nucleotide sequence of SEQ ID NO:55, (iv) a promoter comprising a nucleotide sequence having at least 80% identity with the nucleotide sequence of SEQ ID NO:55, (v) a promoter comprising a nucleotide sequence having at least 90% identity with the nucleotide sequence of SEQ ID NO:55, (vi) a promoter comprising a nucleotide sequence having at least 95% identity with the nucleotide sequence of SEQ ID NO:55, and (vii) a promoter comprising a nucleotide sequence having at least 98% identity with the nucleotide sequence of SEQ ID NO:55.

In another embodiment, the promoter comprises (i) a nucleotide sequence having at least 50% identity with the nucleotide sequence of SEQ ID NO:56, (ii) a promoter comprising a nucleotide sequence having at least 60% identity with the nucleotide sequence of SEQ ID NO:56, (iii) a promoter comprising a nucleotide sequence having at least 70% identity with the nucleotide sequence of SEQ ID NO:56, (iv) a promoter comprising a nucleotide sequence having at least 80% identity with the nucleotide sequence of SEQ ID NO:56, (v) a promoter comprising a nucleotide sequence having at least 90% identity with the nucleotide sequence of SEQ ID NO:56, (vi) a promoter comprising a nucleotide sequence having at least 95% identity with the nucleotide sequence of SEQ ID NO:56, and (vii) a promoter comprising a nucleotide sequence having at least 98% identity with the nucleotide sequence of SEQ ID NO:56.

The coding sequence for a selectable marker encodes a selectable marker. Selectable marker coding sequences are utilized for the selection of transformed cells or tissues. Usually, the selectable marker coding sequences will encode antibiotic resistance, with suitable coding sequences including at least one of coding sequence coding for resistance to the antibiotic spectinomycin, coding sequence for resistance to zeomycin, the streptomycin phosphotransferase (spt) gene coding for streptomycin resistance, the neomycin phosphotransferase (nptii) gene encoding kanamycin or geneticin resistance, the hygromycin phosphotransferase (hpt or aphiv) gene encoding resistance to hygromycin, acetolactate synthase (als) genes or the nourseothricin acetyltransferase (nat) gene encoding resistance to neurseothricin. Alternatively, the plant selectable marker coding sequences will encode herbicide resistance such as resistance to the sulfonylurea-type herbicides, glufosinate, glyphosate, ammonium, bromoxynil, imidazolinones, and 2,4-dichlorophenoxyacetate (2,4-D), including genes coding for resistance to herbicides which act to inhibit the action of glutamine synthase such as phosphinothricin or basta (e.g., the bar gene). See generally, International Publication No. WO 02/36782, U.S. Pat. No. 7,205,453 and U.S. Patent Application Publication Nos. 2006/0218670, 2006/0248616, 2007/0143880 and 20090100536, and the references cited therein. See also, Jefferson et al. (1991); De Wet et al. (1987); Goff et al. (1990); Kain et al. (1995) and Chiu et al.

(1996). This list of selectable marker genes is not meant to be limiting. Any selectable marker gene can be used.

In one embodiment, the coding sequence for the selectable marker is one that is either naturally existent or artificially created and contains at least about 60% GC. In a second embodiment, the coding sequence for the selectable marker is one that is either naturally existent or artificially created and contains about 70% GC. In a third embodiment, the coding sequence for the selectable marker is one that is either naturally existent or artificially created and contains about 75% GC. In one embodiment, at least about 70% of the codon triplets of such coding sequences end with C or G. In another embodiment, more than about 80% of the codon triplets of such coding sequences end with C or G. In one embodiment, the coding sequence for a selectable marker is at least 60% GC, preferably about 70% GC and most preferably about 75% GC in which at least 70% of the codon triplets end with C or G, preferably more than 80% of the codon triplets end with C or G. In one embodiment, such coding sequences are composed of UCG codons in at least about 40% of the total serine (Ser) residues.

In one embodiment, the coding sequence for a selectable marker comprises the nucleotide sequence set forth in SEQ ID NO:6. In another embodiment, the coding sequence for drug resistance comprises the nucleotide sequence set forth in SEQ ID NO:7. In an additional embodiment, the coding sequence for drug resistance comprises the nucleotide sequence set forth in SEQ ID NO:8.

In one embodiment, any transcriptional terminator operable in species of the fungi can be used. Terminators are typically located downstream (3') of the gene, after the stop codon (TGA, TAG or TAA). Terminators play an important role in the processing and stability of RNA as well as in translation. Most, but not all terminators, contain a polyadenylation sequence or cleavage site. Examples of specific polyadenylation sequences are AAUAAA or AAUAAU. These sequences are known as the near upstream elements (NUEs) (Nagaya et al., 2010). NUEs usually reside approximately 30 bp away from a GU-rich region (Mogen et al., 1990; Mogen et al., 1992; Rothnie et al. 1994), known as far upstream elements (FUEs). The FUEs enhance processing at the polyadenylation sequence or cleavage site, which is usually a CA or UA in a U-rich region (Bassett, 2007). Within the terminator, elements exist that increase the stability of the transcribed RNA (Ohme-Takagi et al., 1993; Newman et al., 1993; Gutiérrez et al., 1999) and may also control gene expression (Ingelbrecht, 1989; An et al., 1989).

Nucleic acid hybridization, a technique well known to those of skill in the art of DNA manipulation, can be used to identify other suitable terminators. In accordance with the invention other suitable promoters for use may be obtained by the identification of terminators that selectively hybridize to the promoters described above by hybridization under low stringency conditions, moderate stringency conditions, or high stringency conditions. Selectively hybridizing sequences typically have at least 50% sequence identity, preferably at least 70%, 80% or 90% sequence identity, and most preferably 95%, 98% or 99% sequence identity with each other.

Database searches and homology searches of genome and nucleotide databases identify similar DNA or RNA molecules based on the alignment of nucleotides using algorithms or computer programs and these techniques well known to those of skill in the art. In accordance with the invention other suitable terminators for use may be obtained by the in silico identification of terminators for regulatory sequences with at least 50% sequence identity, preferably at least 70%, 80% or 90% sequence identity, and most preferably 95%, 98% or 99% sequence identity with each other.

A DNA of interest can be added to the polynucleotide construct. The DNA of interest is operatively linked to promoter and a terminator. Any promoter and terminator operable in species of the Pucciniomycotina and Ustilaginomycotina subphyla can be used. In some embodiments, the DNA of interest may be used to insert or modify metabolic pathways, such as fatty acid biosynthesis, lipid biosynthesis, triglyceride biosynthesis, and the like. The DNA of interest may be inserted into the genome of the fungal cells to enhance the bioconversion of renewable resources into high-value products, such as triglycerides, biodiesel, fatty alcohol, vitamins, biosurfactants, lactone, terpenoid and the like.

The DNA of interest can be selected to inhibit expression of a native DNA sequence within a plant's tissues to achieve a desired phenotype. In this case, such inhibition might be accomplished, for example, with transformation of the fungal cell to comprise a promoter linked to an antisense nucleotide sequence, hairpin, RNA interfering or other nucleic acid molecule, such that tissue-preferred expression of the molecule interferes with translation of the mRNA of the native DNA sequence or otherwise inhibits expression of the native DNA sequence in fungal cells. For further description of RNAi techniques, see, e.g., U.S. Pat. Nos. 5,034,323; 6,326,527; 6,452,067; 6,573,099; 6,753,139; and 6,777,588. See also International Patent Publications WO 97/01952, WO 98/36083, WO 98/53083, WO 99/32619 and WO 01/75164; and U.S. Patent Publications 2003/0175965, 2003/0175783, 2003/0180945, 2004/0214330, 2005/0244858, 2005/0277610, 2007/0265220, 2009/0215860, 2009/0308041 and 2010/0058498.

In a second aspect, the present invention provides a method for the transformation of a fungal cell of a species of the Pucciniomycotina and Ustilaginomycotina subphyla. In one embodiment, the fungal cell is a species of the *Rhodosporidium* or *Sporobolomyces* genera. In another embodiment, the fungal cell is a species of the *Ustilago* or *Sporisorium* genera. In a further embodiment, the fungal cell is a species of the *Rhodoturula* or *Pseudozyma* genera. According to this aspect, the method comprises transforming a fungal cell with the polynucleotide construct described herein and selecting a transformed fungal colony. In one embodiment, the transformation method is *Agrobacterium tumefaciens*-mediated transformation (ATMT). In another embodiment, the transformation method is electroporation. In an additional embodiment, the transformation method is transfection. In a further embodiment, the transformation method is biolistic.

For example, the polynucleotide construct may be introduced directly into the genomic DNA of the fungal cell using techniques such as electroporation and microinjection of plant cell protoplasts, or the polynucleotide constructs can be introduced directly to fungal tissue using ballistic methods, such as DNA particle bombardment. Alternatively, the polynucleotide constructs may be combined with suitable T-DNA flanking regions and introduced into a conventional *Agrobacterium tumefaciens* host vector. The virulence functions of the *Agrobacterium tumefaciens* host will direct the insertion of the construct into the fungal cell DNA when the cell is infected by the bacteria. Thus, any method, which provides for effective transformation/transfection may be employed. See, for example, U.S. Pat. Nos. 7,241,937, 7,273,966 and 7,291,765 and U.S. Patent Application Publication Nos. 2007/0231905 and 2008/0010704 and references cited therein. See also, International Published Application Nos. WO 2005/103271 and WO 2008/094127 and references cited therein.

In one embodiment, the transformation step comprises co-culturing the fungal cell with *Agrobacterium tumefaciens* that contains vector comprising the polynucleotide construct. In one embodiment, the co-culturing is performed on a solid co-culturing medium or on a co-culturing membrane that is laid on top of a solid medium. In one embodiment, the selection step is performed by over-laying a solid selection medium on top of the solid co-culturing medium having transformed fungal cells thereon or by transferring the co-culturing membrane having transformed fungal cells thereon to a solid selection medium. In one embodiment, the co-culturing medium and the selection medium contain at least 1.5% agar, preferably between 2% and 3% agar.

In one embodiment, the ATMT embodiment, the method comprises the steps: (a) creating a synthetic DNA construct that comprises (i) a promoter derived from the *Aspergillus, Rhosporidium, Sporobolomyces, Sporisorium, Rhodoturula, Pseudozyma* or *Ustilago* genera operatively linked to (ii) a coding sequence for a selectable marker operatively linked to (iii) a transcriptional terminator that are operatively linked; (b) inserting the DNA construct into a T-DNA binary vector; (c) introducing the resulting T-DNA vector into a strain of *Agrobacterium*; (d) co-culturing the *Agrobacterium* cells with fungal cells on a solid medium, or on a membrane that is laid on top of a solid medium, preferably in the presence of *Agrobacterium* virulence inducer, such as acetosyringone (AS) to transform fungal cells; (e) selecting a transformed colony directly on a solid medium or on a membrane that is laid atop of a solid medium. The selection medium can be further supplemented with agents at a concentration that completely suppress the growth of *Agrobacterium* and non-transformed fungal cells. In one embodiment, the promoter is one described herein. In another embodiment, the coding sequence for a selectable marker is one described herein. In one embodiment, the selection or co-culturing media contains at least about 1.5% agar. In another embodiment, the selection or co-culturing media contains between about 2% and about 3% agar.

Figure 7:
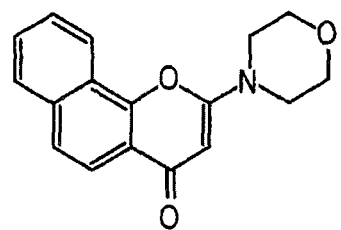
FIG. 7 shows the structure of the DNA-PK inhibitor NU7026 (2-(morpholin-4-yl)-benzo[h]chomen-4-one; 2-(4-morpholinyl)-4H-naphthol [1,2-b] pyran-4-one).

In a third aspect, the present invention provides an improved method for gene targeting in fungi. In particular, a DNA-dependent protein kinase (DNA-PK) inhibitor can be supplemented at a substantial amount to a medium used for transformation. In one embodiment, the DNA-PK inhibitor is NU7026 (2-(morpholin-4-yl)-benzo[h]chomen-4-one; 2-(4-morpholinyl)-4H-naphthol[1,2-b]pyran-4-one; FIG. 7). In another embodiment, the amount of NU7026 in the medium is between about 0.1 µM and about 50 µM. In a further embodiment, the gene targeting requires a homology region of a targeted fungal genomic sequence of at least 50 nucleotides, preferably more than 500 nucleotides. In an additional embodiment, the DNA-PK inhibitor can be used with any transformation protocol, such as ATMT, electroporation, transfection, biolistic and the like.

In a fourth aspect, the present invention provides a method for reducing false transformants in targeted genome. According to this aspect, the method comprises designing a coding sequence for a selectable marker in which the coding sequence contains codon usage preference that matches that of the targeted genome. The method also comprises operatively linking the designed coding sequence to a strong promoter and to a transcriptional terminator to create a construct. The method further comprises transforming a cell of the targeted genome with the construct. Finally, the method comprises selecting transformed cells under maximal concentration of selection agents. In one embodiment, the coding sequence is as described herein. In another embodiment, the strong promoter is as described herein. In a further embodiment, the terminator is one described herein. In one embodiment, the genome is one from a fungal species in the *Ustilago* or *Sporisorium* genera. In another embodiment, the fungal species is a species of the *Rhodosporidium* or *Sporobolomyces* genera. In a further embodiment, the fungal species is a species of the *Rhodoturula* or *Pseudozyma* genera.

The transformed fungi are transferred to standard growing media (e.g., solid or liquid nutrient media, grain, vermiculite, compost, peat, wood, wood sawdust, straw, etc.) and grown or cultivated in a manner known to the skilled artisan.

After the polynucleotide is stably incorporated into transformed fungi, it can be transferred to other fungi by sexual crossing. Any of a number of standard breeding techniques can be used, depending upon the species to be crossed.

It may be useful to generate a number of individual transformed fungi with any recombinant construct in order to recover fungi free from any positional effects. It may also be preferable to select fungi that contain more than one copy of the introduced polynucleotide construct such that high levels of expression of the recombinant molecule are obtained.

It may be desirable to produce fungal lines that are homozygous for a particular gene if possible in the particular species. In some species this is accomplished by the use monosporous cultures. By using these techniques, it is possible to produce a haploid line that carries the inserted gene and then to double the chromosome number either spontaneously or by the use of colchicine. This gives rise to a fungus that is homozygous for the inserted gene, which can be easily assayed for if the inserted gene carries with it a suitable selection marker gene for detection of fungi carrying that gene. Alternatively, fungi may be self-fertilized, leading to the production of a mixture of spores that consists of, in the simplest case, three types, homozygous (25%), heterozygous (50%) and null (25%) for the inserted gene. Although it is relatively easy to score null fungi from those that contain the gene, it is possible in practice to score the homozygous from heterozygous fungi by Southern blot analysis in which careful attention is paid to the loading of exactly equivalent amounts of DNA from the mixed population, and scoring heterozygotes by the intensity of the signal from a probe specific for the inserted gene. It is advisable to verify the results of the Southern blot analysis by allowing each independent transformant to self-fertilize, since additional evidence for homozygosity can be obtained by the simple fact that if the fungi was homozygous for the inserted gene, all of the subsequent fungal lines from the selfed individual will contain the gene, while if the fungus was heterozygous for the gene, the generation grown from the selfed seed will contain null fungal lines. Therefore, with simple selfing one can select homozygous fungal lines that can also be confirmed by Southern blot analysis.

Creation of homozygous parental lines makes possible the production of hybrid fungus and spores that will contain a modified protein component. Transgenic homozygous parental lines are maintained with each parent containing either the first or second recombinant DNA sequence operably linked to a promoter. Also incorporated in this scheme are the advantages of growing a hybrid crop, including the combining of more valuable traits and hybrid vigor.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, *Molecular Cloning* (Cold Spring Harbor Laboratory Press, Cold Spring Harbor, N.Y.); Sambrook et al., 1989, *Molecular Cloning*, 2nd Ed. (Cold Spring Harbor Laboratory Press, Cold Spring Harbor, N.Y.); Sambrook and Russell, 2001, *Molecular Cloning*, 3rd Ed. (Cold Spring Harbor Laboratory Press, Cold Spring Harbor, N.Y.); Ausubel et al., 1992), *Current Protocols in Molecular Biology* (John Wiley & Sons, including periodic updates); Glover, 1985, DNA Cloning (IRL Press, Oxford); Russell, 1984, *Molecular biology of plants: a laboratory course manual* (Cold Spring Harbor Laboratory Press, Cold Spring Harbor, N.Y.); Anand, *Techniques for the Analysis of Complex Genomes*, (Academic Press, New York, 1992); Guthrie and Fink, *Guide to Yeast Genetics and Molecular Biology* (Academic Press, New York, 1991); Harlow and Lane, 1988, *Antibodies*, (Cold Spring Harbor Laboratory Press, Cold Spring Harbor, N.Y.); *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); Riott, *Essential Immunology*, 6th Edition, Blackwell Scientific Publications, Oxford, 1988; Fire et al., *RNA Interference Technology: From Basic Science to Drug Development*, Cambridge University Press, Cambridge, 2005; Schepers, *RNA Interference in Practice*, Wiley-VCH, 2005; Engelke, *RNA Interference (RNAi): The Nuts & Bolts of siRNA Technology*, DNA Press, 2003; Gott, *RNA Interference, Editing, and Modification: Methods and Protocols (Methods in Molecular Biology)*, Human Press, Totowa, N.J., 2004; Sohail, *Gene Silencing by RNA Interference: Technology and Application*, CRC, 2004.

EXAMPLES

The present invention is described by reference to the following Examples, which are offered by way of illustration and are not intended to limit the invention in any manner. Standard techniques well known in the art or the techniques specifically described below were utilized.

Example 1

Culture of Microbial Strains and Basic Molecular Methods

*R. toruloides* strain ATCC10657, ATCC10788 and *R. glutinis* strain ATCC90781 were sourced from the American Type Culture Collections (ATCC). *Ustilago maydis* strain and *Agrobacterium tumefaciens* strain AGL-1 have been described (Ji et al., 2010; Lazo et al., 1991). *Sporisorium scitamineum* haploid S10 is a haploid strain originated from China. *Escherichia coli* strain XL1-Blue was used for routine plasmid manipulation and amplification. *Rhodosporidium* and *U. maydis* were cultured at 28° C. in YPD broth (1% yeast extract, 2% peptone, 2% glucose) or on solid potato-dextrose agar (PDA). *A. tumefaciens* was cultured at 28° C. in either liquid or solid 2YT medium (1.6% tryptone, 1% yeast extract, 0.5% NaCl). *E. coli* was grown in LB broth or on solid LB agar. For lipid production, *R. toruloides* was cultured in liquid accumulation medium as described previously (Wu et al., 2010a) at 30° C. with constant shaking (200 rpm). Antibiotics Hygromycin B, Nourseothricin, Carboxin and Zeocin were purchased from Roche (USA), Werner BioAgents (Germany), Sigma-Aldrich (USA) and Invitrogen (USA), respectively.

Genomic DNA of *R. toruloides* was extracted based on the method described for *U. maydis* (Ji et al., 2010) with some modifications. Briefly, the cell culture at exponential phase was collected and washed with 1 M sorbitol. The cells were resuspended in 0.1 ml of SCS buffer (1 M sorbitol, 20 mM sodium citrate, pH 5.8) and supplemented with glass beads (1 mm in diameter, Sigma-Aldrich, USA). Cells lysis made by vortexing and genomic DNA was isolated after phenol/chloroform extraction and ethanol precipitated. The extracted DNA was quantified with NanoDrop® ND-1000 Spectrophotometer (Nanodrop Technologies, USA) and DNA quality analyzed by agarose gel electrophoresis. For Southern blot analysis, the genomic DNA was digested with BamHI and separated by electrophoresis on 0.8% agarose gels. Southern hybridization was carried out according to the manufacturer's instructions for DIG-High prime DNA labeling and detection starter Kit II (Roche Diagnostics, USA) using DIG-labeled PCR product derived from hpt-3 gene (Roche diagnostics, USA).

T-DNA tagging positions in the genome were determined using either Inverse PCR (Ochman et al., 1988) or Thermal Asymmetric InterLaced PCR (hiTAIL-PCR) (Liu and Chen, 2007; Liu and Whittier, 1995). The oligos HptRU/HptRSL (SEQ ID NO:38/SEQ ID NO:39) and GAPSL/Tnos-Sf (SEQ ID NO:46/SEQ ID NO:47) were used for the first and second round inverse PCR respectively. For HiTAIL-PCR, specific primers Rsp1 (SEQ ID NO:40), Rsp2 (SEQ ID NO:41) and Rsp3 (SEQ ID NO:42) and arbitrary primer LAD1-1 (SEQ ID NO:43) or LAD1-4 (SEQ ID NO:44), AC1 (SEQ ID NO:45). All PCR reactions were carried out using Taq DNA polymerase (Qiagen, USA) in a PTC-200™ Programmable Thermal Controller (BioRad, USA). The specific PCR products were extracted using gel extraction kit (Qiagen) and sequenced with the BigDye method after subcloning into pGTM-T Easy (Promega, USA).

Example 2

DNA Constructs

Oligonucleotides used are SEQ ID NOs:11-47. Oligos LoxP1 (SEQ ID NO:11) and LoxP2 (SEQ ID NO:12) were annealed and ligated with EcoRI/XbaI double digested pPZP200 (Hajdukiewicz et al., 1994) to create pEX0, which contains two Cre recombinase recognition sites (loxP) flanking two unique restriction sites, EcoRV and XhoI. The NcoI site between the gpd promoter and hpt coding sequence in pGH1 (Ji et al., 2010) was abolished by changing to the fourth nucleotide of hpt gene from G to A by oligo-mediated mutagenesis to create pGH4, from which the 1854 bp SpeI-SphI fragment was blunt-ended with T4 DNA polymerase and inserted into the EcoRV site of pEX0 to create pEX1. The whole Pgpd::hpt::T35S cassette from pEX1 was amplified by PCR using oligos RB-S (SEQ ID NO:13) and 35TLU2 (SEQ ID NO:14), digested with PstI, and inserted between the XbaI and PstI site of pPZP200 to create pEX2.

Promoters of the glyceraldehyde phosphate dehydrogenase A (gpdA) and translation elongation factor A (tefA) were amplified from *Aspergillus niger* SG1 genomic DNA using primers GAPU/GAPL (SEQ ID NO:15/SEQ ID NO:16) and TEFU/TEFL (SEQ ID NO:17/SEQ ID NO:18), respectively. A codon-optimized hpt gene (hpt-2) (SEQ ID NO:6) linked to the 35S transcriptional terminator was amplified with primers HPTU (SEQ ID NO:19) and T35SL (SEQ ID NO:20) from a modified pCambia1305.1 vector, which was digested with BspHI and blunt-ended and kinase at the 3' end before individually ligated with the SalI/NcoI double-digested promoter PCR product and EcoRV/XhoI digested pEX0 to create pEX3 and pEX4, respectively. pEX3GPDA-EGFP and pEX4GPDA-EGFP were constructed from pEX3 and pEX4 by inserting a gpdA::egfp:trpC cassette which contains a 884 bp gpdA promoter of *Aspergillus nidulans* from pAN7-1 (GenBank Accession No. Z32698.1) (Punt et al., 1987) driving expression of eGFP, respectively.

pEX2 was digested by PstI, blunt-ended by T4 DNA polymerase and subsequently digested with SpeI, from which the 6.7 kb fragment was ligated with the NcoI-cut, blunt-ended and SpeI-cut pMF2-3c (a generous gift from Prof. Dr. Michael Feldbrügge, Institute for Microbiologym, Universitässtrasse, Germany) to create pEC2. Several restriction sites in pEC2 was removed by self-ligating the NcoI-PmeI double-digested and blunt-ended product to create pEC3. pEC3PgpdU-eGFP was generated by ligation of SacI-PacI digested and blunt-ended pEC3 with the Pgpd$^U$::egfp::Tnos cassette that was amplified using pEX1GPD-eGFP as the template and Pgpd-Sf and Tnos-Pmr as primers. Pgpd$^U$ refers the gap promoter from *U. maydis* (Smith and Leong, 1990); egfp the enhanced Green Fluorescence Protein encoding gene jellyfish *Aequorea victoria* and Tnos the nopaline synthase terminator of *Agrobacterium tumefaciens* (Hentges et al., 2005). Plasmids pEC3PgpdR-hpt3, pEC3PgpdA-hpt3 and pEC3Ptef-hpt3 are derivatives of pEC3PgpdU-eGFP, containing the synthesized hpt gene variant, hpt-3 (SEQ ID NO:7) under the regulation of gpdA promoter originated from *R. toruloides* gpd (gpdA$^{Rt}$) (SEQ ID NO:2), *Aspergillus nidulans* (gpdA$^{An}$) (SEQ ID NO:3), and tef promoter from *Ashbya gossypii* (SEQ ID NO:5) (Steiner and Philippsen, 1994), respectively. FIG. 1 shows some of the constructs used.

Example 3

Transformation of *R. toruloides* Via Electroporation

Protoplasts of *R. toruloides* were prepared according to the method described previously (Heiser, 2000; Kuo et al., 2004) with some modifications. Briefly, fungal cells were digested with lyzing enzymes from *Trichoderma harzianum* (Sigma) and washed with Hepes buffer (1 mM Hepes, 0.6 mannitol, pH7.5). Protoplasts ($1 \times 10^8$) were mixed with plasmid DNA (5 μg), chilled on ice for 10 min, and subjected to electroporation in a BIO-RAD GENE PULSER® II equipped with Controller Plus and Capacitance Extender Plus. A series of parameters were tested using pEC3PgpdU-hpt3 with field strength varied from 1.25 kV/cm to 2.5 kV/cm; capacitor from 10 μF to 50 μF, and resistance from 100Ω to 600Ω. No true transformants were been obtained in several attempts.

Example 4

PEG-Mediated Transformation of *R. toruloides* Protoplasts

PEG-mediated protoplast transformation was performed as described previously (Schulz et al., 1990; Tully and Gilbert, 1985) with some modifications. In brief, exponential phase *R. toruloides* cells cultured in YPD medium were harvested, washed and resuspended with SCS buffer (20 mM Sodium citrate buffer, pH5.8, 1 M sorbitol). The fungal cell wall was degraded using lyzing enzymes from *Trichoderma harzianum* (Sigma) in SCS buffer as a concentration of 10 mg/ml, and mixed gently at room temperature until protoplasts were formed (1.5-2 h). Protoplasts were pelleted, washed twice with SCS and once with STC (10 mM Tris-HCl, pH7.5, 100 mM CaCl$_2$, 1M sorbitol). Protoplasts were resuspended in STC at a concentration of $2 \times 10^8$/ml and kept at −80° C. For transformation, 1-5 μg of DNA (in less than 5 μl) was mixed with 1 μl of heparin (15 mg/ml) and 50 μl of protoplasts. After incubating the mixture in ice bath for 10 min, 500 μl of PEG-4000 (40% w/v in STC) was added, and incubated on ice for 15 min. The protoplasts were mixed with 5 ml of soft agar (0.7% agar in YPD, 1 M sorbitol) that was kept at 45° C. and poured onto a freshly prepared plate containing 10 ml medium that was composed of 1.5% agar in YPD, 1 M sorbitol, 200 μg/ml hygromycin B. Plates were incubated at 28° C. for 5-7 days. Transformation using different plasmids, e.g., pEX2, pEC3PgpdU-hpt3, and PCR products containing the PgpdA$^U$::hpt:Tnos cassette derived from pEX2 or Pgpd$^U$::hpt-3:Tnos cassette derived from pEC3PgpdU-hpt3, failed to generate any transformants.

Example 5

Identification of gpdA from *R. toruloides*

To obtain the sequence of gpdA from *R. toruloides*, degenerate primers Rtgpdf, 5'-AAYGGNTTYGGNCG-NATHGGNCG-3' (SEQ ID NO:21) and Rtgpdr, 5'-CCNACNGCYTTNGCNGCNCCNGT-3' (SEQ ID NO:22), which target the highly conserved motif NGF-GRIGR (SEQ ID NO:23) and TGAAKAVG (SEQ ID NO:24), respectively, were used to amplify a fragment by RT-PCR using total RNA of *R. toruloides* as the template. A BLASTx search confirmed the PCR product encodes the targeted region. To obtain the full-length of RtgpdA gene sequence, oligo pairs Rtgpd-IP2f/Rtgpd-IP1r (SEQ ID NO:26/SEQ ID NO:25) and Rtgpd-IP2f/Rtgpd-IP2r (SEQ ID NO:26/SEQ ID NO:27) were designed according to the above partial genomic DNA sequence and used for 2 inverse PCRs. Clear PCR products of 2.5 kb, 2.8 kb and 1.1 kb could be produced from DNA templates digested with BamHI, EcoRI and PstI, respectively. As a result, a 3568 bp sequenced was obtained. To define the mRNA sequence, 5'RACE and 3'RACE were performed with specific primer Rt007 SEQ ID NO:28) and Rtgpd-IP1r (SEQ ID NO:25), which yielded a PCR product of 0.9 and 0.7 kb, respectively. The full-length mRNA is shown in SEQ ID NO:10. BlastN search of SEQ ID NO:10 revealed it is most related to the gpd of *Ustilago maydis* 521 (Genbank No. UM02491.1) with 81% identity over a region of 810 nucleotides.

Example 6

Analysis of Rtgpd Promoter Activity

As the *Ustilago maydis* gpd gene is highly related *Rhodosporidium toruloides*, we envisioned that *Ustilago maydis* would be a suitable host to analyze the function of the RtgpdA promoter. We serially truncated upstream DNA fragments of RtgpdA, fused in-frame with eGFP coding sequence (Spellig et al., 1996) and integrated to the ip locus of *U. maydis*. Readings of green fluorescence intensity of the transformants are shown in Table 1. Notably, the 791 bp promoter was comparable to the *U. maydis* gpd promoter. Importantly, sequence as short as 176 bp showed fairly strong expression of GFP.

TABLE 1

Deletion Analysis of Rtgpd Promoter

| Length[1] | Relative Fluorescence[2] (%) |
|---|---|
| 176 | 42.2 ± 1.3 |
| 250 | 60.2 ± 7.4 |
| 441 | 31.0 ± 6.5 |
| 612 | 84.3 ± 14.0 |
| 795 | 100.0 ± 13.4 |
| 975 | 87.9 ± 11.0 |
| 1270 | 82.4 ± 8.3 |
| 1429 | 78.5 ± 7.9 |
| Umgpd | 101.9 ± 2.8 |

[1]The length refers to size of the fragment upstream of the transcriptional initiation site.
[2]The 795 bp promoter was set at 100%. Results were the average of triplicates.

Example 7

Design of hpt-2 and hpt-3 for Transformation of Sporisorium scitamineum and R. toruloides Many attempt to transform R. toruloides and Sporisorium scitamineum failed to generate transformants using the pTHR1 and reported transformation protocol (Ji et al., 2010). Interestingly, another transformation vector, pANT-GFP7-1, in which the hpt was under the control of Aspergillus nidulans gpdA promoter and trpC terminator showed much better result (Table 2). However, nearly half of the transformants were false-positives as revealed by Southern blot analysis. Based on this information, we created pEX1GPD-EGFP, in which hpt gene was placed under the control of U. maydis gpd promoter and Cauliflower mosaic virus 35S transcriptional terminator. As expected, transformation efficiency was nearly doubled and false positives further reduced to about 21%. These results indicated that weak expression of selection marker was the cause of low transformation efficiency and high false positives. Accordingly, we focused on further increasing Hpt protein expression by codon optimization. An analysis of the E. coli hpt coding sequence (SEQ ID NO:9) revealed that it has a GC content of 57 0.5%, which is close to that of gpd (gap) gene of U. maydis (GC 58%). Among the 342 codons used, 62.6% ended with C or G. Therefore, we designed a hpt gene variant, hpt-2, which had a higher GC content (62.4%) and 83.3% of the codons end with C or G. As expected, use of hpt-2 lead to drastically increased transformation efficiency and further reduction of false positives in Sporisorium scitamineum.

TABLE 2

Comparison of Selection Markers

| Binary Vector | Selection Marker | Average CFU[1] | GFP Positive (%) |
|---|---|---|---|
| pTHR1 | PTef$^{4g}$::hpt:Ttef$^{4g}$ | 0 | NA |
| pANTGFP7-1 | PgpdA$^{An}$::hpt:trpC$^{An}$* | 9 ± 2 | 54 |
| pEX1GPD-EGFP | Pgpd$^{Um}$::hpt:T35S | 17 ± 5 | 79 |
| pEX3GPDA-EGFP | PgpdA$^{An}$**::hpt-2:T35S | 159 ± 22 | 86 |
| pEX4GPDA-EGFP | PtefA$^{An}$**::hpt-2:T35S | 100 ± 16 | 86 |

[1]Co-cultured was done in IM with 2.5% agar for 63 hr and selected against 300 μg/ml cefotaxome and 200 μg ml$^{-1}$ hygromycin B. Colonies were scored after 7 days in selection medium. CFU means the average number of transformants between three plates ± standard error.
*Derived from gpdA promoter and trpC terminator of A. nidulans.
**Promoters derived from A. niger.

Figure 2D:
Figure 2A:
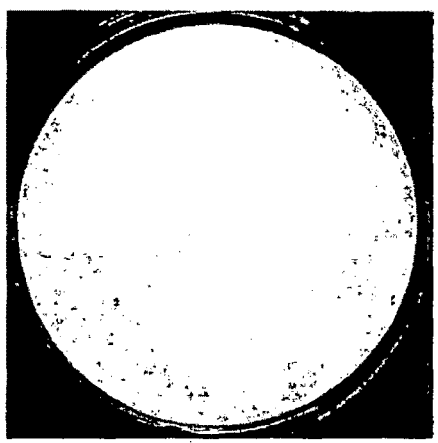
Figure 2B:
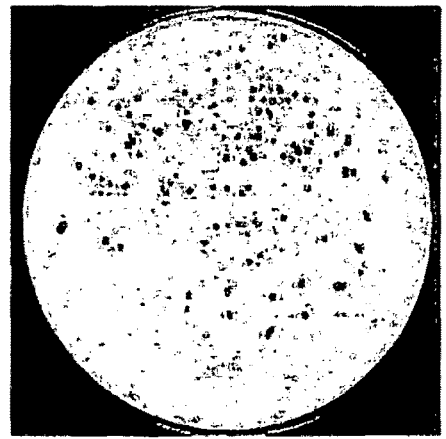
Figure 3A:
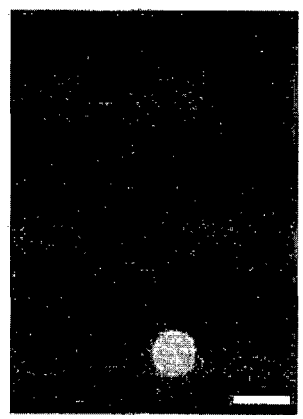
FIGS. 3A and 3B show expression of GFP in hygromycin-resistant colonies.
Figure 3B:

A similar situation was observed in ATMT of R. toruloides. In this case, constructs composing of U. maydis gpd promoter and either hpt or hpt-2 gave poor transformation results with almost 100% false-positives under the selection conditions in which no hygromycin B resistant colonies could be generated (FIGS. 2 and 3).

Figure 4:
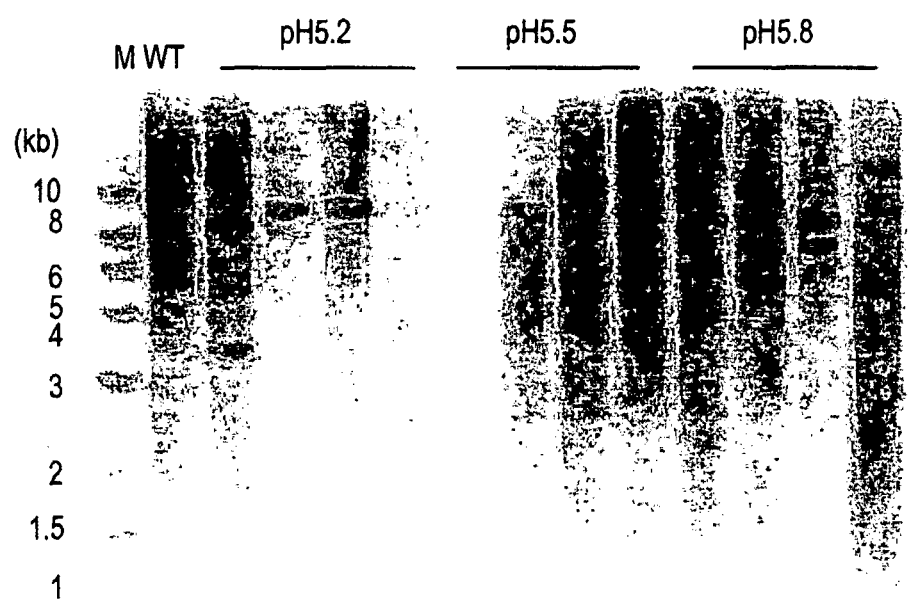
FIG. 4 shows Southern blot of R. toruloides transformants obtained under various co-culture medium pH. WT; wild-type R. toruloides. The blot was probed against hpt-3.
Figure 5:
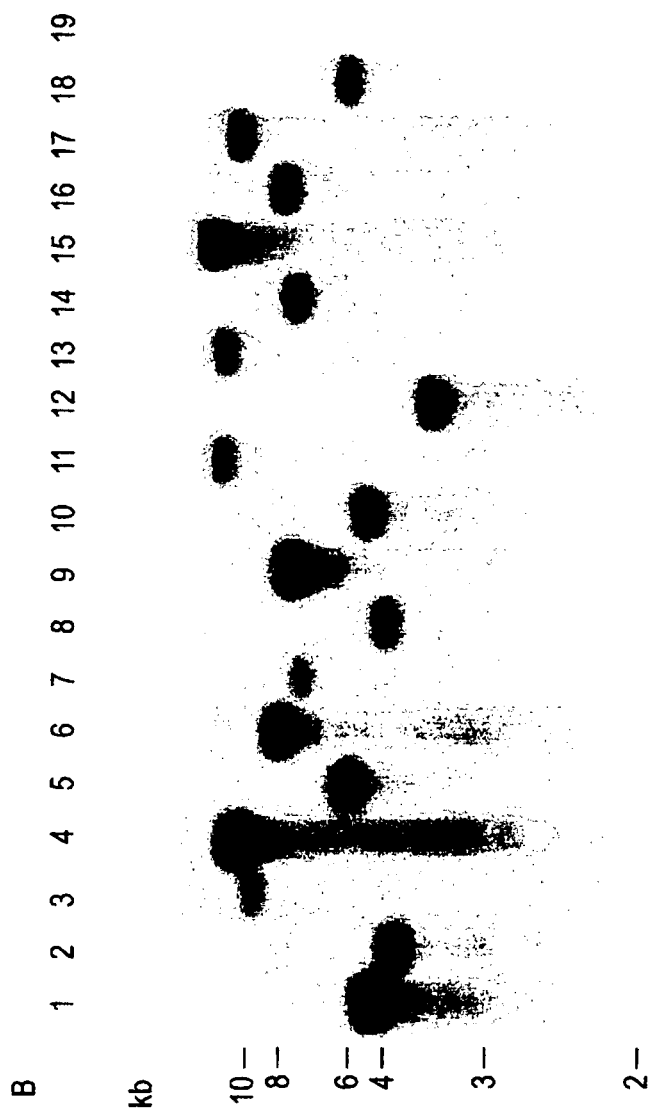
FIG. 5 shows Southern blot analysis of Sporisorium scitamineum transformants. Genomic DNA was digested with BamHI and probed with a [$^{32}$P]-labeled hpt DNA fragment. Lanes 1 to 18 are DNA from putative transformants. Lane 19 is Sporisorium scitamineum wild-type DNA. Molecular markers are indicated on the left.
Figure 6:
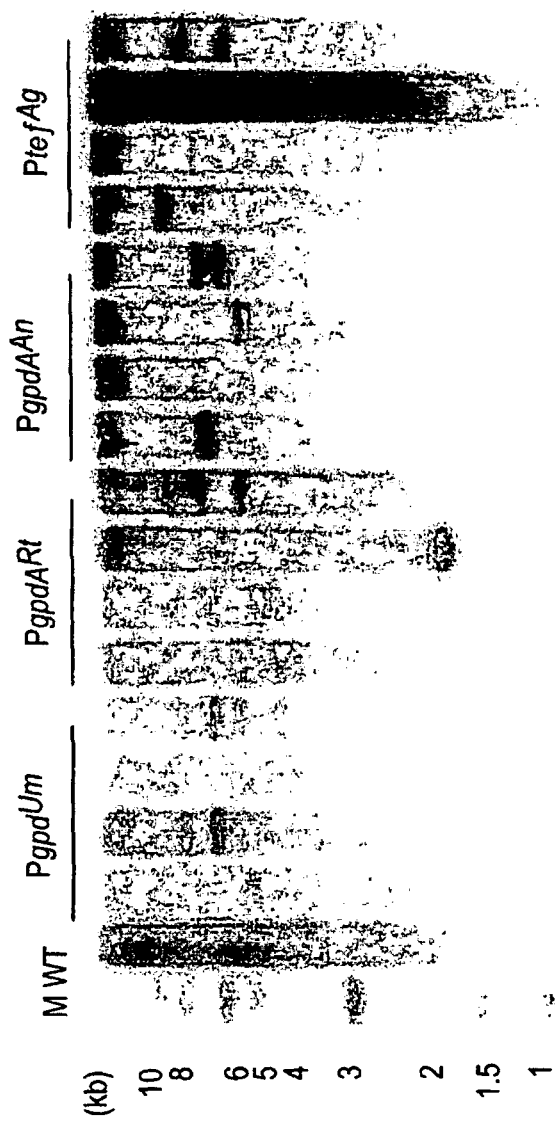
FIG. 6 shows Southern blot of transformants of R. glutenis with different promoters. Pgpd$^{Um}$, PgpdA$^{Rt}$, PgpdA$^{An}$ and Ptef$^{Ag}$ refer to the gpd promoter from Ustilago maydis, R. toruloides, Aspergillus nidulans and Ashibia gossipii, respectively. The blot was probed against hpt-3.

Based on the experience in the transformation of Sporisorium scitamineum realizing the high GC content and codon preference of R. toruloides, we designed hpt-3, with the GC content further increased to 70.4% and with 100% codons ends with C or G. As expected, true transformed colonies were obtained with operatively fused with gpdA, promoter from Ustilago maydis, Aspergillus nudulans or Rhodosporidium toruloides (Table 3). T-DNA constructs containing hpt-2 and hpt-3 was integrated into the genomes (FIGS. 4 and 5). As expected, the constructs with hpt-3 was able to transform R. glutinis ATCC90781.

TABLE 3

Transformation of R. toruloides Using Various Selection Markers

| | CFU/10$^6$ sporidium |
|---|---|
| Pgpd$^{Um}$::hpt-3:T35S | 21 |
| PgpdA$^{An}$::hpt-3:T35S | 824 |
| PgpdA$^{Rt}$::hpt-3:T35S | 1882 |

Both gpd promoter from both gpdA from A. nidulans (PgpdA$^{An}$) and the native RtgpdA promoter (gpdA$^{Rt}$) exhibited high transformation frequencies. However, U. maydis gpd$^{Um}$ was the weaker.

Example 8

Agrobacterium Tumefaciens-Mediated Transformation (ATMT)

Agrobacterium cultures were mixed with R. toruloides at a volume ratio of 2:1 and spread on IM agar medium with 100 μM acetosyringone on a membrane. After co-culture at 24° C. for 2 days, the membrane was transferred to a YPD plate containing 300 μg/ml cefotaxime and 100 μg/ml hygromycin B and plates were incubated at 28° C. for 3-5 days. For Sporisorium scitamineum, cells were cultured in YPD medium until 0.5-0.8 OD600 and 150 μl of which was mixed with 100 μl a pre-induced Agrobacterium culture before being spread evenly onto a 0.45 μm Hybond N membrane disc (Amersham Pharmacia) that was placed on an IM plate. Co-culture was done at 24° C. in the dark for 48-96 hours. Subsequently, membranes were transferred onto a YPD plate containing 300 μml-1 cefotoxime (Sigma-Aldrich) and 50-200 μg ml-1 hygromycin B (Roche) to select for transformants. Both IM and YPD plates contain at least 2.5% agar and should be air-dried for 20-30 minutes before use.

To improve transformation efficiency, several parameters were trialed in the ATMT of Rhodosporidium and Sporisorium scitamineum. Among the environmental factors that significantly influenced transformation efficiency and false-positive rate, membrane type and concentration of solidifying agent and co-culture medium pH ranked high (Tables 4, 5 and 6). Nylon N+ and cellulose acetate membrane exhibited best transformation efficiency while the optimal co-culture pH was found between 5.3-5.7. Agar concentration also had a major effect on transformation efficiency, particularly for Sporisorium scitamineum.

TABLE 4

Effect of Co-Culture pH and Concentration
of Solidifying Agent on Transformation of *Sporisorium scitamineum*

| pH | AS | Agar (%) | CFU/Plate[1] | GFP Positive (%) |
|---|---|---|---|---|
| 5.0 | + | 2.5 | 0 | NA[2] |
|  | − | 2.5 | 0 | NA |
| 5.3 | + | 2.5 | 3 ± 1 | 30% |
|  | − | 2.5 | 0 | NA |
| 5.5 | + | 2.5 | 11 ± 3 | 80% |
|  | − | 2.5 | 0 | NA |
| 5.7 | + | 2.5 | 5 ± 2 | 41% |
|  | − | 2.5 | 0 | NA |
| 5.9 | + | 2.5 | 0 | NA |
|  | − | 2.5 | 0 | NA |
| 5.5 | + | 1.5 | 0 | NA |
| 5.7 | + | 1.5 | 0 | NA |

[1]Co-culture was performed at 24° C. for 52 hr on the IM pH indicated using AGL1 carrying pEX1GPD-eGFP as a donor. Selection was done on YPD medium with 300 μg ml⁻¹ cefotaxome and 200 μg ml⁻¹ hygromycin B. CFU stands for the average number of transformants. Results derived from 3 repeats.
[2]NA: not applicable

TABLE 5

Effects of Co-Culture pH and Concentration
of Solidifying Agent on Transformation of *R. toruloides*

| pH | Agar (%) | AS | CFU/$10^6$ sporidium |
|---|---|---|---|
| 5.2 | 2 | − | 0 |
|  |  | + | 305 |
| 5.3 | 2 | − | 0 |
|  |  | + | 370 |
| 5.4 | 2 | − | 0 |
|  |  | + | 404 |
| 5.5 | 2 | − | 0 |
|  |  | + | 468 |
| 5.6 | 2 | − | 0 |
|  |  | + | 377 |
| 5.7 | 2 | − | 0 |
|  |  | + | 68 |
| 5.8 | 2 | − | 0 |
|  |  | + | 0 |
| 5.5 | 1.5 | + | 242 |
| 5.5 | 2.5 | + | 282 |
| 5.5 | 3 | + | 146 |

Note:
100 μl pre-induced AGL1 cells transformed with pEC3PgpdU-hpt-3 was co-cultured with 100 μl *R. toruloides* (ATCC 10657) and co-cultured on a Nylon N⁺ membrane for 48 hours.

TABLE 6

Effect of Membranes on Transformation Efficiency

| Membrane | CFU/$10^6$ sporidium |
|---|---|
| Whatman Filter paper No. 4 | 0 |
| Nitrocellulose membrane | 0 |
| Acetate cellulose membrane | 383 |
| Nylon N membrane | 0 |
| Nylon N+ membrane | 100 |
| Membrane-free | 375 |

Note:
100 μl pre-induced AGL1 cells transformed with pEC3PgpdU-hpt3 was co-cultured with 100 μl *R. toruloides* (ATCC 10657) and co-cultured on various membranes for 48 hours.

Example 9

Selection Using Nourseothricin

To demonstrate the feasibility to use a natural drug resistance gene in *Rhodosporidium* transformation, we performed ATMT using pNGR1 that has been shown effective in selecting transformants in *U. maydis* (Ji et al., 2010). Using above optimized protocol, many nourseothricin resistant colonies were produced when selected against 50 μg/ml ClonNAT ~80% of them contained the T-DNA as identified by colony PCR (FIG. 2D).

TABLE 7

ATMT Using nat as a Selection Marker

| AS | CFU/$10^6$ sporidium |
|---|---|
| − | 0 |
| + | 46 |

Note:
100 μl pre-induced AGL1 cells transformed with pNGR1 was co-cultured with 100 μl *R. toruloides* (ATCC 10657) and co-cultured on a Nylon N⁺ membrane for 48 hours.

Example 10

Gene Knockout in *U Maydis* cyp1 (um11812) and ptf1 (um02713) genes were chosen for the comparison of gene-targeting frequency, which can be monitored by the loss of ustilagic acids (UA) production and the loss of Fuz⁺ colonies, respectively. Gene deletion constructs, pKOcyp1 and pKOprf1, were made by one-step ligation of four fragments. pKOcyp1 is composed of the 2.0-kb HindIII-PacI fragment containing the Pgpd::hpt cassette, the 8.7 kb NcoI-KpnI fragment from pEX2tk, the 1405 bp NcoI-HindIII and the 1076 bp PacI-KpnI PCR product derived from the upstream and downstream regions of the cyp1 ORF. The oligo pairs Cyp1L-Nf/Cyp1L-Hr (SEQ ID NO:29/SEQ ID NO:30) and Cyp1R-Pf/Cyp1R-Kr (SEQ ID NO:31/SEQ ID NO:32) were used for the amplification of upstream and downstream region, respectively. pKOprf1 was made similarly except the PCR product of oligo pairs Prf1L-Nf/Prf1L-Hr (SEQ ID NO:33/SEQ ID NO:34) and Prf1R-Pf/Prf1R-Kr (SEQ ID NO:35/SEQ ID NO:36) were used as the upstream and downstream homology region, respectively. Correct strains were identified by colony PCR using Taq DNA polymerase based on the size of the expected constructs using oligos LB/Cyp1L-Nf (SEQ ID NO:37/SEQ ID NO:29) and LB/Prf1L-Nf (SEQ ID NO:37/ SEQ ID NO:33) for cyp1Δ and prf1Δ respectively. The same construction and identification techniques were applied to generate other gene deletion mutants in this study.

Example 11

Improving Gene-Targeting Frequency with NU7026

PEG-mediated transformation of *U maydis* spheroplasts were done as described previously (Kämper, 2004). Briefly, the 4.5 kb cyp1 and prf1 gene deletion cassettes were amplified from pKOcyp1 and pKOprf1 using the Expand Long System (Roche Diagnosis, USA) and oligos Cyp1L-Nf/Cyp1R-Kr (SEQ ID NO:29/SEQ ID NO:32) and Prf1L-Nf/Prf1R-Kr (SEQ ID NO:33/SEQ ID NO:36), respectively. The PCR products were gel purified (Qiagen, Germany) and used for transformation. A chemical inhibitor of DNA-dependent protein kinase (DNA-PK), NU7026 (2-(morpholin-4-yl)-benzo[h]chomen-4-one; 2-(4-morpholinyl)-4H-naphthol[1,2-b]pyran-4-one), was added into both the top and bottom regeneration agar media at 1 μM to both bottom and top regeneration media and cultured for 3 days. True gene deletion mutants were confirmed by Southern blotting and fungal colony PCR (out of 288 transformants). In both cyp1 and prf1, gene knockout frequency was increased about 3 folds (Table 8).

TABLE 8

Effects of NU7026 in PEG-Mediated Transformation

| cyp1Δ | | prf1Δ | |
|---|---|---|---|
| Control | NU7026 | Control | NU7026 |
| 5.21% | 16.67% | 9.03% | 26.39% |

Similar results were obtained when knockout was performed via the ATMT transformation (Table 9).

TABLE 9

Effects of NU7026 on Gene Knockout Frequency in ATMT

| Concentration (μM) | cyp1Δ (%) | prf1 Δ (%) |
|---|---|---|
| 0 | 5.2 (749) | 8.5 (837) |
| 0.1 | 8.3 (601) | 11.4 (642) |
| 1 | 18.8 (496) | 25.1 (554) |
| 5 | 10.4 (413) | 12.7 (361) |
| 10 | 8.3 (96) | 8.7 (172) |
| 50 | 7.4 (68) | 8.5 (59) |

Note:
AGL1 strain harboring pKOprf1 and pKOcy11 was co-cultured with U. maydis L8 and SG200 for 2 days in the presence NU7026 at various concentrations. Numbers in brackets indicate the total number of transformants obtained in 5 transformation plates.

Example 12

Analysis of Nucleotide Composition and Codon Usage

The identification of RtgpdA allowed us to analyze the nucleotide composition and codon usage in this important gene that are usually strongly expressed. The ORF has a CG content of 62.6% and 87.3% of the codon triplets end with C or G. Overall, C is much more preferred over G in the $3^{rd}$ nucleotide position accounting for 64.2% of all codons. A notable exception is serine, which is encoded with the UCG codon at frequency of 69.6% (16 out of 23). A similar data was found in 8 other genes of Rhodosporidium toruloides that was listed in the GenBank, including L-phenylalanine ammonia-lyase (GenBank Accession No. E01543.1); orotidine 5'-phosphate decarboxylase (ura3, EU693529.1); cephalosporin esterase (AF025410.1); epoxide hydrolase (EPH1, AY227047.1), rhodotorucine A1 (RHA1, M28121.1); rhodotorucine A2 (RHA2, M28122.1); rhodotorucine A3 (RHA3, M28123.1); D-amino acid oxidase (AF003339.1). Among the 8 genes, GC content is 63% and 82.3% of the codons end with C or G. The preference to C or G at the $3^{rd}$ position is stronger in RtgpdA than the 8 gene average (Table 10). In contrast, the gpd (gap) gene of Ustilago maydis (UM02491.1) has a GC content of 58% and 44.5% of the codons end with C or G. A surprising result was found in the expression of eGFP (SEQ ID NO:48) in Rhodosporidium toruloides. Although it has a CG content of 59.9% and 64.3% of the codons end with C and 26% end with G (total codons ending with C and C 90.3%), no green florescence could be observed when it was driven with the strong RtgpdA promoter. A comparison of codon usage pattern between RtgpdA and eGFP revealed that the preferred codons UCG (Serine), GUC (Valine) and CUC (Leucine) codons were not used in eGFP. Because constructs containing hpt-2 failed to transform Rhodosporidium toruloides, we analyzed the codon usage in htp-2. The codon preferences for proline (CCA), arginine (AGG), serine (AGC) and valine (GUG) were drastically different from that of RtgpdA. The most obvious difference between hpt-2 and hpt-3 is the codon usage for serine (Table 10).

Analysis of three genes available in the Genbank database, translation elongation factor 1-alpha (GenBank: DQ352829.1), gpdA (GenBank: DQ352817.1) and actin (GenBank: FJ 514819.1), showed a similar preference to C or G in codon usage. Mostly notable, UCG is the most preferred codon for serine. To see if Sporobolomyces has similar pattern of codon usage, Glycerol-3-phosphate dehydrogenase, Pyruvate carboxylase (estExt_ Genewise 1.C_20242), gw1.13.90.1 (Protein ID: 5205) Citrate synthase and Protein ID 12137; scaffold_4:2114010-2115782; stearoyl-CoA 9-desaturase activity were retrieved from http colon slash slash genome dot jgi-psf dot org slash Sporo1 slash Sporo1 dot home dot html and analyzed. These four CDS has a CG content of 55.5% and 43.7% of the codons end with C and 19.6% end with G (total codons ending with C and G 63.3%). Similarly, the UCG codon was strongly biased for serine, accounting for 43.1% of the serine codons (Table 10).

Analyses of the codon usage in Pseudozyma species revealed highly similar codon usage pattern to those of Rhodosporidium and Sporisorium scitamineum. For example, the genes of Pseudozymaflocculosa encoding 3 abundant proteins Actin (Genbank No. DQ913895); gpdA (EF030711) and EF1a (GQ922837) have a CG content of 62.95% with 100% isoleucine residues encoded by AUC, 36.5% Serine encoded by UCG; 11.3% serine encoded by UCC and 100% histidine residues encoded by CAC.

TABLE 10

Analysis of codon preferences

| | Preferred codons (%) | | | | | | |
|---|---|---|---|---|---|---|---|
| Amino acids | Hpt-2 | Hpt-3 | RtGpd-A | Rhdospoiridium toruloides | eGFP | Sporobolomyces roseus | Sporisorium scitamineum |
| Ala | GCC(83.8) | GCC(94.6) | GCC(61.5) | GCC(39.8) | GCC(72.7) | GCC(36.4) | GCC(70) |
| | GCU(16.2) | GCG(5.4) | GCG(15.4) | GCG(32.1) | GCG(9) | GCG(16) | GCU(27.5) |
| Cys | UGC(100) | UGC(100) | UGC(100) | UGC(89.4) | UGC(100) | UGC(85.2) | UGC(91.7) |
| Asp | GAC(92.3) | GAC(100) | GAC(96) | GAC(88.2) | GAC(78.3) | GAC(64.9) | GAC(96.1) |
| Glu | GAG(100) | GAG(100) | GAG(100) | GAG(79.7) | GAG(93.8) | GAG(53.5) | GAG(93.4) |

TABLE 10-continued

Analysis of codon preferences

| Amino acids | Preferred codons (%) | | | | | | |
|---|---|---|---|---|---|---|---|
| | Hpt-2 | Hpt-3 | RtGpd-A | Rhdospoiridium toruloides | eGFP | Sporobolomyces roseus | Sporisorium scitamineum |
| Phe | UUC(100) | UUC(100) | UUC(81.8) | UUC(82.6) | UUC(100) | UUC(95.7) | UUC(82.4) |
| Gly | GGC(87.5) | GGC(100) | GGC(55.9) | GGC(62.6) | GGC(86.4) | GGA(52.6) | GGU(58) |
| | GGA(12.5) | | GGU(32.4) | GGA(14.6) | GGG(13.6) | GGT(31) | GGC(33.3) |
| His | CAU(83.3) | CAC(100) | CAC(100) | CAC(84.5) | CAC(86.7) | CAC(82.1) | CAC(100) |
| Ile | AUC(100) | ATC(100) | AUC(90.5) | AUC(83.5) | AUC(92.3) | AUC(82.3) | AUC(87.8) |
| | | | AUU(9.5) | AUU(15.6) | AUU(7.7) | AUU(17) | AUU(12.2) |
| Lys | AAG(100) | AAG(100) | AAG(100) | AAG(93.7) | AAG(95) | AAG(77) | AAG(98.5) |
| Leu | CUC(84.6) | CUC(100) | CUC(76.2) | CUC(67.7) | CUG(81.8) | CUC(69.7) | CUC(72.1) |
| | CUU(15.4) | | CUU(19) | CUU(11.2) | CUC(13.6) | CUU(15.1) | CUG(11.5) |
| Asn | AAC(100) | AAC(100) | AAC(100) | AAC(91.6) | AAC(100) | AAC(90.8) | AAC(92.7) |
| Pro | CCA(86.7) | CCG(100) | CCC(72.7) | CCG(35.9) | CCC(73.3) | CCC(40.2) | CCC(85.4) |
| | | | CCU(27.3) | CCC(32.6) | CCU(20) | CCU(39.4) | CCU(12.5) |
| Gln | CAG(100) | CAG(100) | CAG(100) | CAG(76.4) | CAG(100) | CAA(70.3) | CAG(95.8) |
| Arg | AGG(100) | CGC(100) | CGC(100) | CGC(57) | CGC(100) | CGU(32.3) | CGU(70.3) |
| | | | | CGG(11.4) | | CGC(31.6) | CGC(26.9) |
| Ser | AGC(100) | UCG(100) | UCG(69.6) | UCG(48.6) | AGC(70) | UCG(43.1) | UCG(54.7) |
| | | | UCC(17.4) | UCC(22.9) | UCC(30) | UCC(16.2) | UCC(32.8) |
| Thr | ACC(100) | ACC(100) | ACC(90.9) | ACC(53) | ACC(93.8) | ACC(45.9) | ACC(85.9) |
| | | | ACG(9.1) | ACG(30) | ACU(6.2) | ACU(36.6) | ACU(11.3) |
| Val | GUG(96) | GUC(100) | GUC(83.3) | GUC(75.7) | GUG(65) | GUC(63.8) | GUC(77.5) |
| | GUC(4) | | GUU(13.9) | GUU(10.7) | GUC(20) | GUU(25.9) | GUU(13.8) |
| Tyr | UAC(100) | UAC(100) | UAC(100) | UAC(92.3) | UAC(70.6) | UAC(90.9) | UAC(96.8) |
| GC(%) | 62.4 | 70.5 | 62.6 | 63 | 59.9 | 55.5 | 59.7 |

Example 13

Cloning of Additional Promoters to Drive Strong Gene Expression in Pucciniomycotina and Ustilaginomycotina Subphyla In order to stably express multiple genes in interested species in the Pucciniomycotina and Ustilaginomycotina subphyla, we searched the database for potential genes that may be strongly expressed. Partial genome sequence of Rhodoturula graminis WP1 was released recently (http colon slash slash genome dot jgi-psf dot org slash Rhoba1_1 slash Rhoba1_1 dot home dot html). Scaffold_18: 19976-22436/1-2861 (+) and scaffold_3:1454178-1456821/1-3044 (+) were annotated putatively to encode Glyceraldehyde 3-phosphate dehydrogenases. Alignment of SEQ ID NO: 10 with the predicted CDS of the two sequences revealed that Scaffold_18:19976-22436/1-2861 (+) is likely the homologues of RtgpdA with 81.52% nucleotide identity whereas scaffold_3: 1454178-145682111-3044 (+) shares only 61.38% nucleotide identity. To clone the promoter, the primers of SEQ ID NO:49 and SEQ ID NO:50 were used to PCR amplify Rhodoturula graminis WP1 genomic DNA, which resulted in the amplification of a promoter having SEQ ID NO:51 that was used to fuse with an improved eGFP coding sequence (SEQ ID NO:52) synthesized according to the Rhodosporidium toruloides codon usage in a T-DNA vector (Table 10).

Similarly, we identified the gpdA promoter of Sporobolomyces roseus based on the information in html http colon slash slash genome dot igi-psf dot org slash Sporol slash Sporol dot home dot html. However, the promoter cloned according to the annotation showed no activity to drive expression of SEQ ID NO:52. We thus performed 5' RACE and found that the initiation codon annotated in the database was located in the first intron. The promoter was cloned by PCR using the primers of SEQ ID NO:53 and SEQ ID NO:54, which lead to the cloning of the promoter having SEQ ID NO:55.

Further, we performed 5' RACE to identify the 5'UTRs and translation initiation codon of several other genes. The resultant information was used to clone the corresponding promoters. Among them the Stearoyl-CoA delta9-desaturase gene promoter (SEQ ID NO:56) of *Rhodotorula glutinis* ATCC 204091(GenBank: GL989638.1) was cloned using oligonucleotides of SEQ ID NO:57 and SEQ ID NO:58.

GFP florescence after transformed into *Rhodotorula glutinis* ATCC90781 was observed in promoter listed below although high autofluorescence exist. The GFP intensity was measured using a Tecan Infinate M200 microplate reader. The florescence of control vector with promoter-less GFP gene and nos transcriptional terminator was set at 1. The relative GFP intensity after subtracting WT strain and normalized against cell density (OD600) is listed in Table 11.

TABLE 11

Comparison of Promoter Activity

| Seq ID 4::eGFP:Tnos | Seq ID 2::eGFP:Tnos | Promoter-less eGFP:Tnos | Seq ID 51::eGFP:Tnos | Seq ID 55::eGFP:Tnos | Seq ID 56::eGFP:Tnos |
|---|---|---|---|---|---|
| 15.5 | 96 | 1 | 67.2 | 78 | 86.7 |

Example 14

Transformation of *Sporidiobolus Roseus*, *Pseudozyma Alphidis* and *Rhodotorula Glutinis*

Numerous transformations by ATMT have been successfully done using the improved htp-3 gene. Noticeably, high transformation efficiency with rare false-positive was observed in *Sporobolomyces roseus* FGSC 10293 (IAM 13481) using Pgpd$^{Um}$::hpt-3 as a selection marker. This is in stark contrast to that reported earlier using the same strain and transformation method (Ianiri et al, 2011). Similar results were found with *Pseudozyma aphids* ATCC 32657 and 3 other *Rhodotorula* and *Rhodosporidium* strains (Table 12).

TABLE 12

ATMT of various *Pucciniomycotina* species using 3 versions of hpt

| Strains | Pgpd$^{Um}$::hpt | Pgpd$^{Um}$::hpt-2 | Pgpd$^{Um}$::hpt-3 |
|---|---|---|---|
| *Sporobolomyces roseus* FGSC 10293 (IAM 13481) | NT | NT | >200* (>90%) |
| *Rhodosporidium toruloides* ATCC10657 | 0 | 0 | >100 (>90%) |
| *Rhodotorula glutinis* ATCC90781 | 0 | 0 | >100 (>90%) |
| *Rhodotorula glutinis* ATCC 204091 | 0 | 0 | >20 (>90%) |
| *Pseudozyma aphids* ATCC 32657 | 20-30 (54%)** | NT | >100 (>90%) |

Note:
Co-culture for 3 days and selection was done against 300 μg/ml cefotaxime and 300 μg/ml hygromycin. The rest were selected against 150 μg/ml hygromycin. Numbers in brackets are the false-positive rate as determined by colony PCR of 24 transformants.
FGSC: Fungal Genetics Stock Centre, University of Missouri, USA.
NT: Not tested.
**Colony forming units per 90 mm plate.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

BIBLIOGRAPHY

An, G., et al., 1989. Functional analysis of the 3' control region of the potato wound-inducible proteinase inhibitor II gene. Plant Cell, 1: 115-122.

Bassett, C. L., 2007. Regulation of Gene Expression in Plants: The Role of Transcript Structure and Processing. New York: Springer Press.

Bölker, M., et al., 1995. Tagging pathogenicity genes in *Ustilago maydis* by restriction enzyme-mediated integration (REMI). Mol Gen Genet. 248, 547-52.

Boulton, S., et al., 1999. Interactive effects of inhibitors of poly(ADP-ribose) polymerase and DNA-dependent protein kinase on cellular responses to DNA damage. Carcinogenesis. 20, 199-203.

Boulton, S., et al., 1996. Wortmannin is a potent inhibitor of DNA double strand break but not single strand break repair in Chinese hamster ovary cells. Carcinogenesis. 17, 2285-90.

Bundock, P., et al., 1995. Trans-kingdom T-DNA transfer from *Agrobacterium tumefaciens* to *Saccharomyces cerevisiae*. EMBO J. 14, 3206-14.

Choi, J., et al., 2007. Genome wide analysis of T DNA integration into the chromosomes of *Magnaporthe oryzae*. Molecular Microbiology. 66, 371-382.

Comai, L., et al., 1983. An altered aroA gene product confers resistance to the herbicide glyphosate. Science. 221, 370.

De Groot, M. J. A., et al., 1998. *Agrobacterium tumefaciens*-mediated transformation of filamentous fungi. Nature Biotechnology. 16, 839-842.

de Oliveira, M. L. P., et al., 2009. High-efficiency *Agrobacterium*-mediated transformation of citrus via sonication and vacuum infiltration. Plant Cell Reports. 28, 387-395.

Durant, S., Karran, P., 2003. Vanillins—a novel family of DNA-PK inhibitors. Nucleic Acids Res. 31, 5501-12.

Gietz, R. D. and Woods, R. A., 2002. Transformation of yeast by lithium acetate/single-stranded carrier DNA/polyethylene glycol method. Methods Enzymol. 350, 87-96.

Goldstein, A. L. and McCusker, J. H., 1999. Three new dominant drug resistance cassettes for gene disruption in *Saccharomyces cerevisiae*. Yeast. 15, 1541-1553.

Gutiérrez, R. A., et al., 1999. Current perspectives on mRNA stability in plants: multiple levels and mechanisms of control. Trends Plant Sci, 4: 429-438.

Hajdukiewicz, P., et al., 1994. The small, versatile pPZP family of *Agrobacterium* binary vectors for plant transformation. Plant Molecular Biology. 25, 989-994.

Haughn, G. W., et al., 1988. Transformation with a mutant *Arabidopsis* acetolactate synthase gene renders tobacco resistant to sulfonylurea herbicides. Molecular and General Genetics. 211, 266-271.

Heiser, W. C., 2000. Optimizing electroporation conditions for the transformation of mammalian cells. Methods in Molecular Biology. 130, 117-34.

Hentges, P., et al., 2005. Three novel antibiotic marker cassettes for gene disruption and marker switching in *Schizosaccharomyces pombe*. Yeast. 22, 1013-9.

Hewald, S., et al., 2005. Genetic analysis of biosurfactant production in *Ustilago maydis*. Applied and Environmental Microbiology. 71, 3033.

Hill, J., et al., 1991. DMSO-enhanced whole cell yeast transformation. Nucleic Acids Research. 19, 5791.

Hu, C., et al., 2009. Effects of biomass hydrolysis by-products on oleaginous yeast *Rhodosporidium toruloides*. Bioresour Technol. 100, 4843-7.

Ianiri, G., et al., 2011. Development of resources for the analysis of gene function in Pucciniomycotina red yeasts. Fungal Genetics and Biology. 48, 685-695.

Ingelbrecht, I. L., et al., 1989. Different 3' end regions strongly influence the level of gene expression in plant cells. Plant Cell, 1: 671-680.

Ito, H., et al., 1983. Transformation of intact yeast cells treated with alkali cations. Journal of bacteriology. 153, 163-8.

Ji, L., et al., 2010. A Simplified and efficient method for transformation and gene tagging of *Ustilago maydis* using frozen cells. Fungal Genet Biol. 47, 279-87.

Kämper, J., 2004. A PCR-based system for highly efficient generation of gene replacement mutants in *Ustilago maydis*. Mol Genet Genomics. 271, 103-10.

Khanna, H. K., et al., 2007. Inhibition of *Agrobacterium*-induced cell death by antiapoptotic gene expression leads to very high transformation efficiency of banana. Molecular Plant-Microbe Interactions. 20, 1048-1054.

Kirk, M. P., et al. Dictionary of the Fungi. CABI, Wallingford, 2008, pp. 716.

Krugel, H., et al., 1988. Analysis of the nourseothricin-resistance gene (nat) of *Streptomyces noursei*. Gene. 62, 209-217.

Kück, U. and Hoff, B., 2010. New tools for the genetic manipulation of filamentous fungi. Appl Microbiol Biotechnol. 86, 51-62.

Kuo, C. Y., et al., 2004. Cloning of glyceraldehyde-3-phosphate dehydrogenase gene and use of the gpd promoter for transformation in *Flammulina velutipes*. Appl Microbiol Biotechnol. 65, 593-9.

Lazo, G. R., et al., 1991. A DNA transformation-competent *Arabidopsis* genomic library in *Agrobacterium*. Biotechnology (N Y). 9, 963-7.

Liu, Y. G., Chen, Y., 2007. High-efficiency thermal asymmetric interlaced PCR for amplification of unknown flanking sequences. BioTechniques. 43, 649-50, 652, 654 passim.

Liu, Y. G., Whittier, R. F., 1995. Thermal asymmetric interlaced PCR: automatable amplification and sequencing of insert end fragments from P1 and YAC clones for chromosome walking Genomics. 25, 674-81.

Maehara, T., et al., 2010. Improvement of the Transformation Efficiency of *Flammulina velutipes* Fv-1 Using the Glyceraldehyde-3-phosphate Dehydrogenase Gene Promoter. Bioscience, Biotechnology, and Biochemistry. 74, 2523-2525.

Maier, F. J., Schafer, W., 1999. Mutagenesis via insertional- or restriction enzyme-mediated-integration (REMI) as a tool to tag pathogenicity related genes in plant pathogenic fungi. Biol. Chem. 380, 855-64.

Meng, X., et al., 2009. Biodiesel production from oleaginous microorganisms. Renewable Energy. 34, 1-5.

Meyer, V., 2008. Genetic engineering of filamentous fungi—Progress, obstacles and future trends. Biotechnology Advances. 26, 177-185.

Meyer, V., et al., 2003. Comparison of different transformation methods for *Aspergillus giganteus*. Curr Genet. 43, 371-7.

Mogen, B. D., et al., 1990. Upstream sequences other than AAUAAA are required for efficient messenger RNA 3'-end formation in plants. Plant Cell, 2: 1261-1272.

Mogen, B. D., et al., 1992. Several distinct types of sequence elements are required for efficient mRNA 3' end formation in a pea rbcS gene. Molecular and Cellular Biology, 12: 5406-5414.

Nagaya, S., et al., 2010. The HSP terminator of *Arabidopsis thaliana* Increases Gene Expression in Plant Cells. Plant Cell Physiol, 51: 328-332.

Newman, T. C., et al., 1993. DST sequences, highly conserved among plant SAUR genes, target reporter transcripts for rapid decay in tobacco. Plant Cell, 5: 701-14.

Ochman, H., et al., 1988. Genetic applications of an inverse polymerase chain reaction. Genetics. 120, 621-3.

Ohme-Takagi, M., et al., 1993. The effect of sequences with high AU content on mRNA stability in tobacco. Proc Natl Acad Sci USA, 90: 11811-5.

Pfeifer, T. A., et al., 1997. Baculovirus immediate-early promoter-mediated expression of the Zeocin™ resistance gene for use as a dominant selectable marker in Dipteran and Lepidopteran insect cell lines. Gene. 188, 183-190.

Punt, P. J., et al., 1987. Transformation of *Aspergillus* based on the hygromycin B resistance marker from *Escherichia coli*. Gene. 56, 117-124.

Rosenzweig, K. E., et al., 1997. Radiosensitization of human tumor cells by the phosphatidylinositol3-kinase inhibitors wortmannin and LY294002 correlates with inhibition of DNA-dependent protein kinase and prolonged G2-M delay. Clin Cancer Res. 3, 1149-56.

Rothnie, H. M., et al., 1994. The contribution of AAUAAA and the upstream element UUUGUA to the efficiency of mRNA 3'-end formation in plants. EMBO (Eur Mol Biol Organ) J, 13: 2200-2210.

Schulz, B., et al., 1990. The b alleles of *U. maydis*, whose combinations program pathogenic development, code for polypeptides containing a homeodomain-related motif. Cell. 60, 295-306.

Scorer, C. A., et al., 1994. Rapid Selection Using G418 of High Copy Number Transformants of *Pichia pastoris* for High ℓ evel Foreign Gene Expression. Nature Biotechnology. 12, 181-184.

Skalitzky, D. J., et al., 2003. Tricyclic benzimidazoles as potent poly(ADP-ribose) polymerase-1 inhibitors. J Med Chem. 46, 210-3.

Smith, G. and Jackson, S., 1999. The DNA-dependent protein kinase. Genes & development. 13, 916.

Smith, T. L. and Leong, S. A., 1990. Isolation and characterization of a *Ustilago maydis* glyceraldehyde-3-phosphate dehydrogenase-encoding gene. Gene. 93, 111-7.

Soltani, J., et al., *Agrobacterium*-mediated transformation of non-plant organisms. In: T. Tzfira, V. Citovsky, Eds.), *Agrobacterium*: from biology to biotechnology. Springer press, New York, USA, 2008, pp. 649-675.

Spellig, T., et al., 1996. Green fluorescent protein (GFP) as a new vital marker in the phytopathogenic fungus *Ustilago maydis*. Mol Gen Genet. 252, 503-9.

Steiner, S, and Phillippsen P, 1994. Sequence and promoter analysis of the highly expressed TEF gene of the filamentous fungus *Ashbya gossypii*. Mol Gen Genet. 242, 263-271.

Sweigard, J. A., et al., 1998. *Magnaporthe grisea* pathogenicity genes obtained through insertional mutagenesis. Mol Plant Microbe Interact. 11, 404-12.

Takeno, S., et al., 2005. Transformation of oil-producing fungus, *Mortierella alpina* 1S-4, using Zeocin, and application to arachidonic acid production. Journal of bioscience and bioengineering. 100, 617-622.

Teichmann, B., et al., 2010. Molecular characterization of the biocontrol activity of *Pseudozyma flocculosa*. Phytopathology. 100.

Tentori, L., et al., 2002. Potential clinical applications of poly(ADP-ribose) polymerase (PARP) inhibitors. Pharmacol Res. 45, 73-85.

Tully, M. and Gilbert, H. J., 1985. Transformation of *Rhodosporidium toruloides*. Gene. 36, 235-40.

Turgeon, B. G., et al., 2010. Protoplast transformation of filamentous fungi. Methods in molecular biology. 638, 3-19.

van Attikum, H., et al., 2001. Non-homologous end-joining proteins are required for *Agrobacterium* T-DNA integration. Embo J. 20, 6550-8.

van Attikum, H., et al., 2003. The *Arabidopsis* AtLIG4 gene is required for the repair of DNA damage, but not for the integration of *Agrobacterium* T-DNA. Nucleic Acids Res. 31, 4247-55.

Vega, J. M., et al., 2008 Improvement of *Agrobacterium*-mediated transformation in Hi-II maize (*Zea mays*) using standard binary vectors. Plant cell reports. 27, 297-305.

Veuger, S. J., et al., 2003. Radiosensitization and DNA repair inhibition by the combined use of novel inhibitors of DNA-dependent protein kinase and poly(ADP-ribose) polymerase-1. Cancer Res. 63, 6008-15.

Willmore, E., et al., 2004. A novel DNA-dependent protein kinase inhibitor, NU7026, potentiates the cytotoxicity of topoisomerase II poisons used in the treatment of leukemia. Blood. 103, 4659-65.

Wu, S, and Letchworth, G. J., 2004. High efficiency transformation by electroporation of *Pichia pastoris* pretreated with lithium acetate and dithiothreitol. BioTechniques. 36, 152-155.

Wu, S., et al., 2010a. Phosphate-limitation mediated lipid production by *Rhodosporidium toruloides*. Bioresour Technol. 101, 6124-9.

Wu, S., et al., 2010b. Microbial lipid production by *Rhodosporidium toruloides* under sulfate-limited conditions. Bioresour Technol.

Ye, X. and Gilbertson, L., use of multiple transformation enhancer sequences to improve plant transformation efficiency. EP Patent 2,038,420, 2009.

Zhao, X., et al., 2010a. Lipid production by *Rhodosporidium toruloides* Y4 using different substrate feeding strategies. J Ind Microbiol Biotechnol.

Zhao, X., et al., 2010b. Lipid production from Jerusalem artichoke by *Rhodosporidium toruloides* Y4. J Ind Microbiol Biotechnol. 37, 581-5.

---

What is claimed is:

1. A polynucleotide construct comprising a promoter operatively linked to a coding sequence for a selectable marker operatively linked to a transcriptional terminator, wherein the promoter is from a fungal species selected from the group of a species of the *Aspergillus* genus, a species of the *Rhodosporidium* genus; a species in the *Sporobolomyces* genus; a species in the *Rhodotorula* genus and wherein the polynucleotide construct provides efficient selection of a fungal cell of the Pucciniomycotina and Ustilaginomycotina subphyla, transformed by the insertion of said polynucleotide into said fungal cell.

2. The construct of claim 1, wherein the coding sequence encodes a protein that confers resistance to an antibiotic.

3. The construct of claim 1, wherein the coding sequence encodes a protein that confers resistance to a herbicide.

4. The construct of claim 1, wherein the coding sequence is selected from the group consisting of a coding sequence comprising the nucleotide sequence set forth in SEQ ID NO:6, a coding sequence comprising the nucleotide sequence set forth in SEQ ID NO:7 and a coding sequence comprising the nucleotide sequence set forth in SEQ ID NO:8.

5. The construct of claim 1, wherein the coding sequence for a selectable marker is at least 60% GC, preferably about 70% GC and most preferably about 75% GC; wherein at least 70% of the codon triplets end with C or G, preferably more than 80% of the codon triplets end with C or G.

6. The construct of claim 1, wherein the coding sequence for a selectable marker is composed of UCG codons in at least 40% of the serine residues.

7. The construct of claim 1, wherein the promoter is from a gene encoding glyceraldehyde 3-phosphate dehydrogenase (gpd) or from a gene encoding protein translation elongation factor (tef).

8. The construct of claim 1, wherein the promoter is selected from the group consisting of a promoter comprising the nucleotide sequence set forth in SEQ ID NO:1, a promoter comprising the nucleotide sequence set forth in SEQ ID NO:2, a promoter comprising the nucleotide sequence set forth in SEQ ID NO:3, a promoter comprising the nucleotide sequence set forth in SEQ ID NO:4, a promoter comprising the nucleotide sequence set forth in SEQ ID NO:5; a promoter comprising the nucleotide sequence set forth in SEQ ID NO:51, a promoter comprising the nucleotide sequence set forth in SEQ ID NO:55 and a promoter comprising the nucleotide sequence set forth in SEQ ID NO:56.

9. The construct of claim 1, wherein the fungal cell is a species of the *Rhodosporidium, Sporisorium, Ustilago, Rhodoturula, Pseudozyma* or *Sporobolomyces (Sporidiobolus)* genus.

10. A nucleic acid construct comprising a promoter operatively linked to an heterologous DNA of interest, wherein the promoter is selected from the group consisting of:
(i) a promoter comprising the nucleotide sequence of SEQ ID NO:2, SEQ ID NO:51, SEQ ID NO:55 or SEQ ID NO:56;
(ii) a promoter comprising a nucleotide sequence having at least 50% identity with the nucleotide sequence of SEQ ID NO:2, SEQ ID NO:51, SEQ ID NO:55 or SEQ ID NO:56;
(iii) a promoter comprising a nucleotide sequence having at least 60% identity with the nucleotide sequence of SEQ ID NO:2, SEQ ID NO:51, SEQ ID NO:55 or SEQ ID NO:56;
(iv) a promoter comprising a nucleotide sequence having at least 70% identity with the nucleotide sequence of SEQ ID NO:2, SEQ ID NO:51, SEQ ID NO:55 or SEQ ID NO:56;
(v) a promoter comprising a nucleotide sequence having at least 80% identity with the nucleotide sequence of SEQ ID NO:2, SEQ ID NO:51, SEQ ID NO:55 or SEQ ID NO:56;
(vi) a promoter comprising a nucleotide sequence having at least 90% identity with the nucleotide sequence of SEQ ID NO:2, SEQ ID NO:51, SEQ ID NO:55 or SEQ ID NO:56;
(vii) a promoter comprising a nucleotide sequence having at least 95% identity with the nucleotide sequence of SEQ ID NO:2, SEQ ID NO:51, SEQ ID NO:55 or SEQ ID NO:56; and
(viii) a promoter comprising a nucleotide sequence having at least 98% identity with the nucleotide sequence of SEQ ID NO:2 SEQ ID NO:51, SEQ ID NO:55 or SEQ ID NO:56,
wherein the promoter causes DNA transcription when said nucleic acid construct is inserted into a fungal species selected from the group consisting of a species of the *Ustilago* genus, a species of the *Aspergillus* genus, a species of the *Rhodosporidium* genus, a species of *Rhodotorula* genus, a species of *Pseudozyma* genus and a species of *Sporobolomyces (Sporidiobolus)* genus.

11. A method for transformation of a fungal cell of a species of the Pucciniomycotina and Ustilaginomycotina subphyla which comprises:
(a) transforming a fungal cell with the construct of claim 1 and
(b) selecting a transformed fungal colony.

12. The method of claim 11, wherein the transformation comprises the step of co-culturing said fungal cell with *Agrobacterium tumefaciens* that contains a vector comprising said construct and wherein the co-culturing is performed on a solid co-culturing medium or on a co-culturing membrane that is laid on top of a solid medium.

13. The method of claim 12, wherein the selection is performed by over-laying a solid selection medium on top of the solid co-culturing medium or by transferring the co-culturing membrane to a solid selection medium.

14. The method of claim 13, wherein the co-culturing medium and the solid selection medium contain at least 1.5% agar.

15. The method of claim 11, wherein the fungal cell is a species of the *Rhodosporidium, Rhodotorula, Pseudozyma, Sporisorium,* or *Sporobolomyces* genera.

16. The method of claim 13, wherein the co-culturing medium and the solid selection medium each contains between 2% and 3% agar.

17. A method for transformation of a fungal cell of a species of the Pucciniomycotina and Ustilaginomycotina subphyla which comprises:
(a) transforming a fungal cell with the construct of claim 10, wherein the construct of claim 10 further comprises a coding sequence for a selectable marker, and
(b) selecting a transformed fungal colony with a concentration of a selection agent sufficient to completely suppress the growth of non-transformed cells, wherein the selectable marker confers resistance to the selection agents.

\* \* \* \* \*

SEQUENCE LISTING

```
<160> NUMBER OF SEQ ID NOS: 58

<210> SEQ ID NO 1
<211> LENGTH: 597
<212> TYPE: DNA
<213> ORGANISM: Ustilago maydis

<400> SEQUENCE: 1
gattagatct tgctgatagg caggtttgct tggagaatgg ggggaaaaga ctgaccgaag      60
aaacagcgag atctagaagt gataagcgga aagaatctga cttgctgtga tcagcagcca     120 atttttttt cgtttttttt ttttcactcc acatcgtcgt gcgtgcacgg tctgcatgtg      180
taaattgtat tcatcgaaag ccacagttga atacatcagc ccgatgtgga tttcgaaaac    240
caattaatct tggaattcac gcgctcagat cagtccatag agtcgacttc ggctgtttcc    300
aagagcttct tctctgcgag gtggttgccc gtgtttctcg ctgggaaaaa aggatcgatt    360
attattcgct tctacctcgc tcgcaccctt ggcctgctga aggaaacagc gccgagactc    420
```

-continued

```
ggtcacggtt gctgggctcc gtgttgatgc tgggacggcg caaagtgggg cccgcgcact      480
cttcgagcca aggacctcac tcttcaagaa caagcgctgt cgccatcgtc ttcttctttc      540
tgctccacca tcgaatcttt ctttctcgtt tcgaaaccaa aacactcttc caccatg        597
```

<210> SEQ ID NO 2
<211> LENGTH: 1434
<212> TYPE: DNA
<213> ORGANISM: Rhodosporidium toruloides

<400> SEQUENCE: 2

```
ctgcagaact acgccctctc acacccaact tccgactcga ccggcggtac gagcacgacc      60
tacttctact gcctgccatc gacatccggg cgggtcgctg cctaccctgt gcgttctgcg     120
ccctccctcg tctcgggagg cagtgtctga cagaagcttt gcgcgcagta ccccgtcaag     180
atgcaactct acgcaacgtt cggcacagaa gtcgccaagc tccgcgcatc gccgcctcaa     240
gctctcgcgc tgcccgacgg tgtcgtctat tacgaggcgg agaagctcga gttgccggct     300 tgccagcgg cggtcaaggt tgaggtggag acggagaagg cgggagtagc ggggaggac      360 aatgaggcga agggtgagat ggtgctggtg gagactctta cggtggagca ggaggagatt     420
gaattgggct cgggagtcgt gcagattgag gagtcgttgc tcgtcaagct ggaggtcagc     480
ggctgatcct tccgttcgtt gcaaggatcg tctgcatgtt tcgcttctct caatgacaca     540
acctggagag cgctcccgtc agcgagaatc gaggacattc gcagctcgt gagcaagcgg     600 aggtgcgagg ctccctcgaa agctgcgcct cttcagacgg cttgttctct cctgctctgg     660
tgggctggcc tgacatgtaa tgtgctccgc cgcaagtccg tcgtcggtct caattcgacg     720
ttgaaagggc atagcgcaag gaagaaccct ctgcggacat gcagaattac tggctcgcct     780
gctccttcgt ctactggaat aagtcctgtc tcgttaaagc cccaacgtcg tttttcgacg     840
tttgtaaggc gcaagaggtg ctatgggcta cgcaggaagc tgagaggaca tagaagtcgg     900
gggaggaacg gcgcagagcg gcagttgcgg aagcatgagg aaagcgagac ggtccagcat     960
ctgcagcgcc aatccgcaat ctcctggttg agcctgcacc ggaagcgtcg gaacagtatg    1020
cgcagagtcg aacgcaagta agaaagacgc accctcacac tcgcttactt cgagccatac    1080
aacggatcaa agctgcgcgt atctcggctt gtaagggccg gaaagcaacc tcggagatgg    1140
acacgtcaca tcaccaactt atcgatctcg gccgtcgacg tcgcagagag ggcgagagaa    1200
gcggtgaagg agggaaacaa ccctcgaga gcatgatccg accgaatctg cagcgcagga    1260
agccgttaca agcccgcctc gagcgcaggt cgggtccagc cggggacga aacgcgcgag    1320 gctgattcgt gagcgaagga agccgcatcg acaagttcgc tcccctttgc cctctttccc    1380
atcacccgtt ctcgccttac ccgctcagaa caacaccaga tcactcacaa tgtc          1434
```

<210> SEQ ID NO 3
<211> LENGTH: 888
<212> TYPE: DNA
<213> ORGANISM: Aspergillus nidulans

<400> SEQUENCE: 3

```
ctgtacagtg accggtgact ctttctggca tgcggagaga cggacggacg cagagagaag      60
ggctgagtaa taagcgccac tgcgccagac agctctggcg gctctgaggt gcagtggatg     120
attattaatc cggaccggc cgcccctccg ccccgaagtg gaaaggctgg tgtgcccctc      180
gttgaccaag aatctattgc atcatcggag aatatggagc ttcatcgaat caccggcagt     240
```

```
aagcgaagga gaatgtgaag ccaggggtgt atagccgtcg gcgaaatagc atgccattaa      300
cctaggtaca gaagtccaat tgcttccgat ctggtaaaag attcacgaga tagtaccttc      360
tccgaagtag gtagagcgag tacccggcgc gtaagctccc taattggccc atccggcatc      420
tgtagggcgt ccaaatatcg tgcctctcct gctttgcccg gtgtatgaaa ccggaaaggc      480
cgctcaggag ctggccagcg gcgcagaccg ggaacacaag ctggcagtcg acccatccgg      540
tgctctgcac tcgacctgct gaggtccctc agtccctggt aggcagcttt gcccgtctg      600 tccgcccggt gtgtcggcgg ggttgacaag gtcgttgcgt cagtccaaca tttgttgcca      660
tattttcctg ctctccccac cagctgctct tttcttttct ctttcttttc ccatcttcag      720
tatattcatc ttcccatcca agaaccttta ttcccctaa gtaagtactt tgctacatcc      780
atactccatc cttcccatcc cttattcctt tgaaccttc agttcgagct ttcccacttc      840
atcgcagctt gactaacagc taccccgctt gagcagacat caccatgg                  888
```

```
<210> SEQ ID NO 4
<211> LENGTH: 617
<212> TYPE: DNA
<213> ORGANISM: Aspergillus niger

<400> SEQUENCE: 4
gtcgacgaga tcgtaggagt gagtacccgg cgtgatggag ggggagcacg ctcattggtc       60
cgtacggcag ctgccgaggg ggagcaggag atccaaatat cgtgagtctc ctgctttgcc      120
cggtgtatga aaccggaaag gactgctggg gaactgggga gcggcgcaag ccgggaatcc      180
cagctgacaa ttgacccatc ctcatgccgt ggcagagctt gaggtagctt ttgccccgtc      240
tgtctccccg gtgtgcgcat tcgactgggc gcggcatctg tgcctcctcc aggagcggag      300
gacccagtag taagtaggcc tgacctggtc gttgcgtcag tccagaggtt ccctccccta      360
ccctttttct acttcccctc ccccgccgct caacttttct ttcccttta ctttctctct      420 ctcttcctct tcatccatcc tctcttcatc acttccctct tcccttcatc caattcatct      480
tccaagtgag tcttcctccc catctgtccc tccatctttc ccatcatcat ctcccctccc      540
agctcctccc ctcctctcgt ctcctcacga agcttgacta accattaccc cgccacatag      600
acacatctaa accatgg                                                    617
```

```
<210> SEQ ID NO 5
<211> LENGTH: 388
<212> TYPE: DNA
<213> ORGANISM: Ashibia gossipii

<400> SEQUENCE: 5
cactatacgt gcctcgtccc cgccgggtca cccggccagc gacatggagg cccagaatac       60
cctccttgac agtcttgacg tgcgcagctc aggggcatga tgtgactgtc gcccgtacat      120
ttagcccata catccccatg tataatcatt tgcatccata cattttgatg gccgcacggc      180
gcgaagcaaa aattacggct cctcgctgca gacctgcgag cagggaaacg ctcccctcac      240
agacgcgttg aattgtcccc acgccgcgcc cctgtagaga aatataaaag gttaggattt      300
gccactgagg ttcttctttc atatacttcc ttttaaaatc ttgctaggat acagttctca      360
catcacatcc gaacataaac aaccatgg                                        388
```

```
<210> SEQ ID NO 6
<211> LENGTH: 1026
<212> TYPE: DNA
<213> ORGANISM: Artificial Sequence
```

```
<220> FEATURE:
<223> OTHER INFORMATION: synthetic hpt-2 coding sequence

<400> SEQUENCE: 6
atgaagaagc cagagcttac cgccaccagc gtggagaagt tcctcatcga gaagttcgat      60
agcgtgagcg atctcatgca gctcagcgag ggcgaggaga gcagggcctt cagcttcgat     120
gtgggcggca ggggctacgt gctcagggtg aacagctgcg ccgatggctt ctacaaggat     180
aggtacgtgt acaggcattt cgccagcgcc gccctcccaa tcccagaggt gctcgacatc     240
ggcgagttca gcgagagcct cacctactgc atcagcagga gggctcaggg cgtgaccctc     300
caggatctcc cagagaccga gcttccagcc gtgctccagc cagtggccga ggctatggat     360
gccatcgccg ccgccgatct cagccagacc agcggcttcg cccattcgg cccacagggc      420 atcggccagt acaccacctg agggattc atctgcgcca tcgccgatcc acatgtgtac      480
cattggcaga ccgtgatgga tgataccgtg agcgccagcg tggcccaggc cctcgatgag     540
cttatgctct ggggcgagga ttgcccagag gtgaggcatc tcgtccatgc cgatttcggc     600
agcaacaacg tgctcaccga taacggcagg atcaccgccg tgatcgactg gagcgaggcc     660
atgttcggcg atagccagta cgaggtggcc aacatcttct tctggaggcc ctggctcgcc     720
tgcatggagc agcagaccag gtacttcgag aggaggcacc ctgagcttgc tggaagccca     780
aggctcaggg cctacatgct caggatcggc ctcgatcagc tctaccagag cctcgtggat     840
ggcaacttcg atgatgctgc ttgggctcag ggtaggtgcg atgccatcgt gaggagcgga     900
gccggcaccg tgggcaggac ccagatcgcc aggaggagcg ccgccgtgtg gaccgatggc     960
tgcgtggagg tgctcgccga tagcggcaac aggaggccaa gcaccaggcc aagggccaag    1020
aagtga                                                                1026

<210> SEQ ID NO 7
<211> LENGTH: 1026
<212> TYPE: DNA
<213> ORGANISM: Artificial Sequence
<220> FEATURE:
<223> OTHER INFORMATION: synthetic hpt-3 coding sequence

<400> SEQUENCE: 7
atgaagaagc cggagctcac cgccacctcg gtcgagaagt tcctcatcga gaagttcgac      60
tcggtctcgg acctcatgca gctctcggag ggcgaggagt cgcgcgcctt ctcgttcgac     120
gtcggcggcc gcggctacgt cctccgcgtc aactcgtgcg ccgacggctt ctacaaggac     180
cgctacgtct accgccactt cgcctcggcc gccctcccga tcccggaggt cctcgacatc     240
ggcgagttct cggagtcgct cacctactgc atctcgcgcc gcgcccaggg cgtcacc ctc    300 caggacctcc cggagaccga gctcccggcc gtcctccagc cggtcgccga ggcgatggac     360
gccatcgccg ccgccgacct ctcgcagacc tcgggcttcg cccgttcgg cccgcagggc      420 atcggccagt acaccacctg gcgcgacttc atctgcgcca tcgccgaccc gcacgtctac     480
cactggcaga ccgtcatgga cgacaccgtc tcggcctcgg tcgcccaggc cctcgacgag     540
ctcatgctct ggggccgagga ctgcccggag gtccgccacc tcgtccacgc cgacttcggc     600
tcgaacaacg tcctcaccga caacggccgc atcaccgccg tcatcgactg gtcggaggcc     660
atgttcggcg actcgcagta cgaggtcgcc aacatcttct tctggcgccc gtggctcgcc     720
tgcatggagc agcagacccg ctacttcgag cgccgccacc cggagctcgc cggctcgccg     780
cgcctccgcg cctacatgct ccgcatcggc ctcgaccagc tctaccagtc gctcgtcgac     840
```

| | |
|---|---|
| ggcaacttcg acgacgccgc ctgggcgcag ggccgctgcg acgccatcgt ccgctcgggc | 900 |
| gccggcaccg tcggccgcac ccagatcgcc cgccgctcgg ccgccgtctg gaccgacggc | 960 |
| tgcgtcgagg tcctcgccga ctcgggcaac cgccgcccgt cgacccgccc gcgcgccaag | 1020 |
| gagtag | 1026 |

<210> SEQ ID NO 8
<211> LENGTH: 573
<212> TYPE: DNA
<213> ORGANISM: Unknown
<220> FEATURE:
<223> OTHER INFORMATION: nat coding sequence

<400> SEQUENCE: 8

| | |
|---|---|
| atgggtacca ctcttgacga cacggcttac cggtaccgca ccagtgtccc gggggacacc | 60 |
| gaggccatcg aggcactgga tgggtccttc accaccgaca ccgtcttccg cgtcaccgcc | 120 |
| accggggacg gcttcaccct gcgggaggtg ccggtggacc cgcccctgac caaggtgttc | 180 |
| cccgacgacg aatcggacga cgaatcggac gacggggagg acgcgacccc ggactcccgg | 240 |
| acgttcgtcg cgtacgggga cgacggcgac ctggcgggct tcgtggtcgt ctcgtactcc | 300 |
| ggctggaacc gccggctgac cgtcgaggac atcgaggtcg ccccggagca ccgggggcac | 360 |
| ggggtcgggc gcgcgttgat ggggctcgcg acggagttcg cacgcgagcg gggcgccggg | 420 |
| cacctctggc tggaggtcac caacgtcaac gcaccggcga tccacgcgtg ccggcggatg | 480 |
| gggttcaccc tctgcggcct ggacaccgcc ctgtacgacg gcaccgcctc ggacggcgag | 540 |
| caggcgctct acatgggcat gccctgcccc taa | 573 |

<210> SEQ ID NO 9
<211> LENGTH: 1026
<212> TYPE: DNA
<213> ORGANISM: Escherichia coli

<400> SEQUENCE: 9

| | |
|---|---|
| atgaaaaagc ctgaactcac cgcgacgtct gtcgagaagt ttctgatcga aaagttcgac | 60 |
| agcgtctccg acctgatgca gctctcggag ggcgaagaat ctcgtgcttt cagcttcgat | 120 |
| gtaggagggc gtggatatgt cctgcgggta aatagctgcg ccgatggttt ctacaaagat | 180 |
| cgttatgttt atcggcactt tgcatcggcc gcgctcccga ttccggaagt gcttgacatt | 240 |
| ggggagttta gcgagagcct gacctattgc atctcccgcc gtgcacaggg tgtcacgttg | 300 |
| caagacctgc ctgaaaccga actgcccgct gttctacaac cggtcgcgga gctatggat | 360 |
| gcgatcgctg cggccgatct tagccagacg agcgggttcg gcccattcgg accgcaagga | 420 |
| atcggtcaat acactacatg gcgtgatttc atatgcgcga ttgctgatcc ccatgtgtat | 480 |
| cactggcaaa ctgtgatgga cgacaccgtc agtgcgtccg tcgcgcaggc tctcgatgag | 540 |
| ctgatgcttt gggccgagga ctgccccgaa gtccggcacc tcgtgcacgc ggatttcggc | 600 |
| tccaacaatg tcctgacgga caatggccgc ataacagcgg tcattgactg agcgaggcg | 660 |
| atgttcgggg attcccaata cgaggtcgcc aacatcttct tctggaggcc gtggttggct | 720 |
| tgtatggagc agcagacgcg ctacttcgag cggaggcatc cggagcttgc aggatcgcca | 780 |
| cgactccggg cgtatatgct ccgcattggt cttgaccaac tctatcagag cttggttgac | 840 |
| ggcaatttcg atgatgcagc ttgggcgcag ggtcgatgcg acgcaatcgt ccgatccgga | 900 |
| gccgggactg tcgggcgtac acaaatcgcc cgcagaagcg cggccgtctg gaccgatggc | 960 |
| tgtgtagaag tactcgccga tagtggaaac cgacgcccca gcactcgtcc gagggcaaag | 1020 |

```
aaatag                                                            1026
```

<210> SEQ ID NO 10
<211> LENGTH: 1181
<212> TYPE: DNA
<213> ORGANISM: Rhodosporidium toruloides

<400> SEQUENCE: 10

```
atcacccgtt ctcgccttac ccgctcagaa caacaccaga tcactcacaa tgtctgccgg     60
aaagggatct gtcaacgtcg gaatcaacgg cttcggtcgc atcggccgca tcgtcctccg    120
caacgccatt gagcacggcg atgctcgcgt tgttgccatc aacgacccett tcatcgacct   180 tgagtacatg gtctacatgt tcaagtacga ctcgacccac ggtcgcttca agggcaccat    240
tgaggccaag gacggcaagc tcgtcgtcga cggccacgct atcgacgtct acaacgagaa    300
ggaccccgcc tcgatcccct ggtccaagtc gggcgccgac tacgtcgtcg agtcgaccgg    360
tgtcttcacc accaaggaga aggctggcct tcacttgaag ggcggtgcca agaaggtcgt    420
catctcggcg ccttccgctg acgcccccat gtacgtctgc ggtgtcaacc tcgacaagta    480
caaccccgcc gactcggtca tctcgaacgc ctcgtgcacc accaactgcc ttgcgccccct   540 cgccaaggtc atcaacgaca gttcggcat cgtcgagggt ctcatgacca ccgtccacgc     600
cacgaccgcg acgcagaaga ccgtcgacgg cccttcggcc aaggactggc gcggtggccg    660
cgctgcggct gccaacatca tccccctcgtc gaccggtgcc gccaaggccg tcggcaaggt   720
catccccgag ctcaacggca agctcaccgg catggctttc cgcgtcccca ccaccgacgt    780
ctcggttgtc gacctcaccg tccgccttga aagggcgcc tcgtacgacc agatcaagca     840
gaccatccgc gaggccgcca acggtgagct caagggcatc ctcgagtaca ccgaggacgc    900
gctcgtctca accgactttg tcggccacac cgcctcgtcc atcttcgacg cgtcggctgg    960
tatcgccctc aacgacaact tgtcaagct cgtctcgtgg tacgacaacg agtacgggta    1020
ctccccgccg cgttgtcgacc tcctcgtttt cgtggctaag caggacgccg ccggtggcaa   1080
gctctaagcg gtttctgtag actcccgcct tcctctagcc tagcctcttc gcttcttcca   1140
ctgcgcagtt tgagtgaatg cgtaaaattc agttcacagc c                       1181
```

<210> SEQ ID NO 11
<211> LENGTH: 89
<212> TYPE: DNA
<213> ORGANISM: Artificial Sequence
<220> FEATURE:
<223> OTHER INFORMATION: oligonucleotide containing LoxP site

<400> SEQUENCE: 11

```
aattcaataa ataacttcgt ataatgtatg ctatacgaag ttatctcgag atatcataac     60
ttcgtataat gtatgctata cgaagttat                                       89
```

<210> SEQ ID NO 12
<211> LENGTH: 89
<212> TYPE: DNA
<213> ORGANISM: Artificial Sequence
<220> FEATURE:
<223> OTHER INFORMATION: oligonucleotide containing LoxP site

<400> SEQUENCE: 12

```
ctagataact tcgtatagca tacattatac gaagttatga tatctcgaga taacttcgta     60
tagcatacat tatacgaagt tatttattg                                       89
```

-continued

<210> SEQ ID NO 13
<211> LENGTH: 20
<212> TYPE: DNA
<213> ORGANISM: Artificial Sequence
<220> FEATURE:
<223> OTHER INFORMATION: oligonucleotide PCR primer

<400> SEQUENCE: 13
cctgtggttg gcatgcacat                                           20

<210> SEQ ID NO 14
<211> LENGTH: 48
<212> TYPE: DNA
<213> ORGANISM: Artificial Sequence
<220> FEATURE:
<223> OTHER INFORMATION: oligonucleotide PCR primer

<400> SEQUENCE: 14
aaaggcgcgc cttaattaag gactagtcaa tgtactgaat taacgccg             48

<210> SEQ ID NO 15
<211> LENGTH: 30
<212> TYPE: DNA
<213> ORGANISM: Artificial Sequence
<220> FEATURE:
<223> OTHER INFORMATION: oligonucleotide PCR primer

<400> SEQUENCE: 15
aaagtcgacg agatcgtagg agtgagtacc                                30

<210> SEQ ID NO 16
<211> LENGTH: 31
<212> TYPE: DNA
<213> ORGANISM: Artificial Sequence
<220> FEATURE:
<223> OTHER INFORMATION: oligonucleotide PCR primer

<400> SEQUENCE: 16
aaaaccatgg tttagatgtg tctatgtggc g                              31

<210> SEQ ID NO 17
<211> LENGTH: 43
<212> TYPE: DNA
<213> ORGANISM: Artificial Sequence
<220> FEATURE:
<223> OTHER INFORMATION: oligonucleotide PCR primer

<400> SEQUENCE: 17
aaactcgaga ctagtcacta tacgtgcctc gtccccgccg ggt                  43

<210> SEQ ID NO 18
<211> LENGTH: 36
<212> TYPE: DNA
<213> ORGANISM: Artificial Sequence
<220> FEATURE:
<223> OTHER INFORMATION: oligonucleotide PCR primer

<400> SEQUENCE: 18
aaaccatggt gacggttgtg aatgaactcg aagttc                         36

<210> SEQ ID NO 19
<211> LENGTH: 28
<212> TYPE: DNA
<213> ORGANISM: Artificial Sequence
<220> FEATURE:
<223> OTHER INFORMATION: oligonucleotide PCR primer

```
<400> SEQUENCE: 19
aaaatcatga agaagccaga gcttaccg                                          28

<210> SEQ ID NO 20
<211> LENGTH: 33
<212> TYPE: DNA
<213> ORGANISM: Artificial Sequence
<220> FEATURE:
<223> OTHER INFORMATION: oligonucleotide PCR primer

<400> SEQUENCE: 20
aaaactagtt aattcggggg atctggattt tag                                    33

<210> SEQ ID NO 21
<211> LENGTH: 23
<212> TYPE: DNA
<213> ORGANISM: Artificial Sequence
<220> FEATURE:
<223> OTHER INFORMATION: oligonucleotide PCR primer
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 21
aayggnttyg gncgnathgg ncg                                               23

<210> SEQ ID NO 22
<211> LENGTH: 23
<212> TYPE: DNA
<213> ORGANISM: Artificial Sequence
<220> FEATURE:
<223> OTHER INFORMATION: oligonucleotide PCR primer
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 22
```
ccnacngcyt tngcngcncc ngt                                              23

<210> SEQ ID NO 23
<211> LENGTH: 8
<212> TYPE: PRT
<213> ORGANISM: Rhodosporidium toruloides

<400> SEQUENCE: 23

Asn Gly Phe Gly Arg Ile Gly Arg
1               5

<210> SEQ ID NO 24
<211> LENGTH: 8
<212> TYPE: PRT
<213> ORGANISM: Rhodosporidium toruloides

<400> SEQUENCE: 24

Thr Gly Ala Ala Lys Ala Val Gly
1               5

<210> SEQ ID NO 25
<211> LENGTH: 20
<212> TYPE: DNA
<213> ORGANISM: Artificial Sequence
<220> FEATURE:
<223> OTHER INFORMATION: oligonucleotide PCR primer

<400> SEQUENCE: 25
tgtcttcacc accaaggaga                                                  20

<210> SEQ ID NO 26
<211> LENGTH: 20
<212> TYPE: DNA
<213> ORGANISM: Artificial Sequence
<220> FEATURE:
<223> OTHER INFORMATION: oligonucleotide PCR primer

<400> SEQUENCE: 26
agctatcgag cgagaaacgt                                                  20

<210> SEQ ID NO 27
<211> LENGTH: 21
<212> TYPE: DNA
<213> ORGANISM: Artificial Sequence
<220> FEATURE:
<223> OTHER INFORMATION: oligonucleotide PCR primer

<400> SEQUENCE: 27
tgagtacaac gagttcccac a                                                21

<210> SEQ ID NO 28
<211> LENGTH: 19
<212> TYPE: DNA
<213> ORGANISM: Artificial Sequence
<220> FEATURE:
<223> OTHER INFORMATION: oligonucleotide PCR primer

<400> SEQUENCE: 28
agccatgccg gtgagcttg                                                   19

<210> SEQ ID NO 29
<211> LENGTH: 29
<212> TYPE: DNA
<213> ORGANISM: Artificial Sequence
<220> FEATURE:
<223> OTHER INFORMATION: oligonucleotide PCR primer

<400> SEQUENCE: 29
tttccatggc gaagtcatcc tgtcctcat                                              29

<210> SEQ ID NO 30
<211> LENGTH: 28
<212> TYPE: DNA
<213> ORGANISM: Artificial Sequence
<220> FEATURE:
<223> OTHER INFORMATION: oligonucleotide PCR primer

<400> SEQUENCE: 30
tttaagcttc tttgccaagt tcgacctg                                               28

<210> SEQ ID NO 31
<211> LENGTH: 31
<212> TYPE: DNA
<213> ORGANISM: Artificial Sequence
<220> FEATURE:
<223> OTHER INFORMATION: oligonucleotide PCR primer

<400> SEQUENCE: 31
aaattaatta aacgccatag tgttccatgt c                                           31

<210> SEQ ID NO 32
<211> LENGTH: 29
<212> TYPE: DNA
<213> ORGANISM: Artificial Sequence
<220> FEATURE:
<223> OTHER INFORMATION: oligonucleotide PCR primer

<400> SEQUENCE: 32
aaaggtaccg tcgacatgga taggcacga                                              29

<210> SEQ ID NO 33
<211> LENGTH: 29
<212> TYPE: DNA
<213> ORGANISM: Artificial Sequence
<220> FEATURE:
<223> OTHER INFORMATION: oligonucleotide PCR primer

<400> SEQUENCE: 33
tttccatggc gtcgctctta catcacgaa                                              29

<210> SEQ ID NO 34
<211> LENGTH: 29
<212> TYPE: DNA
<213> ORGANISM: Artificial Sequence
<220> FEATURE:
<223> OTHER INFORMATION: oligonucleotide PCR primer

<400> SEQUENCE: 34
tttaagctta ggacgcttga tatggttgg                                              29

<210> SEQ ID NO 35
<211> LENGTH: 30
<212> TYPE: DNA
<213> ORGANISM: Artificial Sequence
<220> FEATURE:
<223> OTHER INFORMATION: oligonucleotide PCR primer

<400> SEQUENCE: 35
ttttaattaa caagctcttt tgcaaccctc                                             30

<210> SEQ ID NO 36

```
<211> LENGTH: 29
<212> TYPE: DNA
<213> ORGANISM: Artificial Sequence
<220> FEATURE:
<223> OTHER INFORMATION: oligonucleotide PCR primer

<400> SEQUENCE: 36
tttggtacca gcagtttcgc ttccgaata                                              29

<210> SEQ ID NO 37
<211> LENGTH: 22
<212> TYPE: DNA
<213> ORGANISM: Artificial Sequence
<220> FEATURE:
<223> OTHER INFORMATION: oligonucleotide PCR primer

<400> SEQUENCE: 37
ggcaggatat attgtggtgt aa                                                     22

<210> SEQ ID NO 38
<211> LENGTH: 21
<212> TYPE: DNA
<213> ORGANISM: Artificial Sequence
<220> FEATURE:
<223> OTHER INFORMATION: oligonucleotide PCR primer

<400> SEQUENCE: 38
gagtcgctca cctactgcat c                                                      21

<210> SEQ ID NO 39
<211> LENGTH: 20
<212> TYPE: DNA
<213> ORGANISM: Artificial Sequence
<220> FEATURE:
<223> OTHER INFORMATION: oligonucleotide PCR primer

<400> SEQUENCE: 39
agcgactggt agagctggtc                                                        20

<210> SEQ ID NO 40
<211> LENGTH: 19
<212> TYPE: DNA
<213> ORGANISM: Artificial Sequence
<220> FEATURE:
<223> OTHER INFORMATION: oligonucleotide PCR primer

<400> SEQUENCE: 40
caggccgcag agggtgaac                                                         19

<210> SEQ ID NO 41
<211> LENGTH: 22
<212> TYPE: DNA
<213> ORGANISM: Artificial Sequence
<220> FEATURE:
<223> OTHER INFORMATION: oligonucleotide PCR primer

<400> SEQUENCE: 41
ggttcagggg gagatgtggg ag                                                     22

<210> SEQ ID NO 42
<211> LENGTH: 19
<212> TYPE: DNA
<213> ORGANISM: Artificial Sequence
<220> FEATURE:
<223> OTHER INFORMATION: oligonucleotide PCR primer

<400> SEQUENCE: 42
```

```
gtaccggcgc gcccacctg                                              19
```

<210> SEQ ID NO 43
<211> LENGTH: 33
<212> TYPE: DNA
<213> ORGANISM: Artificial Sequence
<220> FEATURE:
<223> OTHER INFORMATION: oligonucleotide PCR primer
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (27)..(29)
<223> OTHER INFORMATION: n is a, c, g, or t

<400> SEQUENCE: 43

```
acgatggact ccagagcggc cgcvnvnnng gaa                              33
```

<210> SEQ ID NO 44
<211> LENGTH: 34
<212> TYPE: DNA
<213> ORGANISM: Artificial Sequence
<220> FEATURE:
<223> OTHER INFORMATION: oligonucleotide PCR primer
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (28)..(30)
<223> OTHER INFORMATION: n is a, c, g, or t

<400> SEQUENCE: 44

```
acgatggact ccagagcggc cgcbdnbnnn cggt                             34
```

<210> SEQ ID NO 45
<211> LENGTH: 16
<212> TYPE: DNA
<213> ORGANISM: Artificial Sequence
<220> FEATURE:
<223> OTHER INFORMATION: oligonucleotide PCR primer

<400> SEQUENCE: 45

```
acgatggact ccagag                                                 16
```

<210> SEQ ID NO 46
<211> LENGTH: 20
<212> TYPE: DNA
<213> ORGANISM: Artificial Sequence
<220> FEATURE:
<223> OTHER INFORMATION: oligonucleotide PCR primer

<400> SEQUENCE: 46

```
agatctcgct gtttcttcgg                                             20
```

<210> SEQ ID NO 47
<211> LENGTH: 30
<212> TYPE: DNA
<213> ORGANISM: Artificial Sequence
<220> FEATURE:
<223> OTHER INFORMATION: oligonucleotide PCR priimer

<400> SEQUENCE: 47

```
tttccgcggt cgaatttccc cgatcgttca                                  30
```

<210> SEQ ID NO 48
<211> LENGTH: 807
<212> TYPE: DNA
<213> ORGANISM: Artificial Sequence
<220> FEATURE:
<223> OTHER INFORMATION: coding sequence for eGFP with C-terminal 2X HA
and 6X His tag

<400> SEQUENCE: 48

| atggcggatc ctgtgagcaa gggcgaggag ctgttcaccg ggtggtgcc catcctggtc | 60 |
| gagctggacg gcgacgtaaa cggccacaag ttcagcgtgt ccggcgaggg cgagggcgat | 120 |
| gccacctacg gcaagctgac cctgaagttc atctgcacca ccggcaagct gcccgtgccc | 180 |
| tggcccaccc tcgtgaccac cctgacctac ggcgtgcagt gcttcagccg ctaccccgac | 240 |
| cacatgaagc agcacgactt cttcaagtcc gccatgcccg aaggctacgt ccaggagcgc | 300 |
| accatcttct tcaaggacga cggcaactac aagacccgcg ccgaggtgaa gttcgagggc | 360 |
| gacaccctgg tgaaccgcat cgagctgaag ggcatcgact tcaaggagga cggcaacatc | 420 |
| ctggggcaca agctggagta caactacaac agccacaacg tctatatcat ggccgacaag | 480 |
| cagaagaacg gcatcaaggt gaacttcaag atccgccaca acatcgagga cggcagcgtg | 540 |
| cagctcgccg accactacca gcagaacacc cccatcggcg acggccccgt gctgctgccc | 600 |
| gacaaccact acctgagcac ccagtccgcc ctgagcaaag accccaacga aaagcgcgat | 660 |
| cacatggtcc tgctggagtt cgtgaccgcc gccgggatca ctctcggcat ggacgagctg | 720 |
| tacaagttaa ttaactaccc ctatgatgta cctgactatg cataccctta tgatgtacca | 780 |
| gactatgctc accatcacca ccatcac | 807 |

<210> SEQ ID NO 49
<211> LENGTH: 32
<212> TYPE: DNA
<213> ORGANISM: Artificial Sequence
<220> FEATURE:
<223> OTHER INFORMATION: oligonucleotide PCR primer

<400> SEQUENCE: 49

| aaaggcgcgc ctacgtctac gtcaagggca at | 32 |

<210> SEQ ID NO 50
<211> LENGTH: 29
<212> TYPE: DNA
<213> ORGANISM: Artificial Sequence
<220> FEATURE:
<223> OTHER INFORMATION: oligonucleotide PCR primer

<400> SEQUENCE: 50

| aaaccatggt tcgagctgga gaaaggtgg | 29 |

<210> SEQ ID NO 51
<211> LENGTH: 963
<212> TYPE: DNA
<213> ORGANISM: Rhodoturula grammis

<400> SEQUENCE: 51

| ggcgcgccta cgtctacgtc aagggcaatg ccgacgtgac caaggccatc ggccaggacc | 60 |
| tcgccttctt ctcggtccct gtcgagctcg gcgtgcgtcc cgccgctctc tctctctctt | 120 |
| tctctcggcc gcgcctcacg tgatccacga cgtcgtactg acccttgcga atgtgcgcgc | 180 |
| ccgcagccca acgcgtcga aaggtgcac ccgctcggcg acctgacggc gttcgagaag | 240 |

```
gagctcctcg aggcgtgcct cggcgagctg cccgggtcca tctccaaggg cgagtcgttc    300
atccagggct ccaagctctg actcgccggc gcatcgacgg gcgcgagcca caaggcgagg    360
atgtgagagg aggcgtttcc tccaccttgg accccatctg ccgcctccct ttctctctct    420
ttctttccct tcctctctct ctctctctct ctcgttctcc tccttctggg cctctcggac    480
ctcttcctcg ccgtcgactc gtgaaaatgc agtgcgcgtt tctgtacctt gtcctgcgag    540
agagatctgg ttctgcgagg gtgagtcgtt gccttggccg tggcacgcct cgccgcagcg    600
agagagaaga ggccacggtc caggacgacg acgacgagga ggaagcgcaa aaggcgagac    660
accgagtgcc atcgattccc cgctcgaacc tgctcacggc tgtcgaaggc ggtgcgccac    720
ggtgcttgcg ggagcgaaag caagctggcg tcgtcctctt gaactggttc gagtccgtga    780
gggcggcgac gagaactcag gcgaggtgct cgcgtcggaa caagccgggc ttgtggtcga    840
gggagcgaga gcgaggcagc gccgtcgtcg ccgaggcaag agcggcatcg acaagttggc    900
ccgtcgcctc tcgctccctc ttctcctcct cccaccacca cctttctcca gctcgaacca    960
tgg                                                                  963

<210> SEQ ID NO 52
<211> LENGTH: 720
<212> TYPE: DNA
<213> ORGANISM: Artificial Sequence
<220> FEATURE:
<223> OTHER INFORMATION: synthetic eGFP coding sequence

<400> SEQUENCE: 52
atggtctcga agggcgagga gctcttcacc ggcgtcgtcc cgatcctcgt cgagctcgac     60
ggcgacgtca acggccacaa gttctcggtc tcgggcgagg gcgagggcga cgccacctac    120
ggcaagctca ccctcaagtt catctgcacc accggcaagc tccgtcccgt ggccgaccc    180 ctcgtcacca ccctcaccta cggcgtccag tgcttctcgc gctacccgga ccacatgaag    240
cagcacgact tcttcaagtc ggccatgccg gagggctacg tccaggagcg caccatcttc    300
ttcaaggacg acggcaacta caagaccgc gccgaggtca agttcgaggg cgacaccctc    360
gtcaaccgca tcgagctcaa gggcatcgac ttcaaggagg acggcaacat cctcggccac    420
aagctcgagt acaactacaa ctcgcacaac gtctacatca tggccgacaa gcagaagaac    480
ggcatcaagg tcaacttcaa gatccgccac aacatcgagg acggctcggt ccagctcgcc    540
gaccactacc agcagaacac cccgatcggc gacggccegg tcctcctccc ggacaaccac    600
tacctctcga cccagtcggc cctctcgaag acccgaacg agaagcgcga ccacatggtc    660
ctcctcgagt tcgtcaccgc cgccggcatc accctcggca tggacgagct ctacaagtag    720

<210> SEQ ID NO 53
<211> LENGTH: 40
<212> TYPE: DNA
<213> ORGANISM: Artificial Sequence
<220> FEATURE:
<223> OTHER INFORMATION: oligonucleotide PCR primer

<400> SEQUENCE: 53
aaaggcgcgc cgaagttata cctcagaggt ctcaaaaacg                           40

<210> SEQ ID NO 54
<211> LENGTH: 35
<212> TYPE: DNA
<213> ORGANISM: Artificial Sequence
<220> FEATURE:
<223> OTHER INFORMATION: oligonucleotide PCR primer
```

<400> SEQUENCE: 54
aaaccatggt gttttgtaga gaaggagtgg agggg                                35

<210> SEQ ID NO 55
<211> LENGTH: 1009
<212> TYPE: DNA
<213> ORGANISM: Sporobolomyces roseus

<400> SEQUENCE: 55
ggcgcgccga agttatacct cagaggtctc aaaaacgaaa aagtcatgca agaatctcct      60
ttgacgtgag ggttatttct cttcctctag tagtctacga gaatcgcaaa gatcggaaaa    120
ctgatgcatc tttgtgttca cgggttagcg atttgatctt ttcgattccc aaaatcgtat    180
cgttcctgtc gcagggaact acgctcaaag ccggcactct gatcatcacg ggagtgagtt    240
ttgagctctc cctctatgag agtgcaaggt tcgtcgctga tggtgtaatc cgctcatgcc    300
ttcccctcta cctctccctt tgtccattct ctctactacg gttgtcacat cttccttctc    360
cgacagaccc cgcacggaat tggagcgtac tcgaatcctc cggaattctt caaggacgga    420
gacgtcttca gggtcgagat ctcggggagc atcgggagtt tggtcaacaa gatcgaatat    480
gaaaagtaga taatccgtta ctcaggtcaa tggtatggct tcgaagatgc tggaatcagc    540
cggaaagcaa agctggagag aaaaatcgag attgcgaaac gtgcgatgtc atttcgtttc    600
gagctcgcaa ccatctcgta tccctctgag ctacatacaa acgtcactac ggcctcggag    660
tgactccctg cgagcggatt gaaggagatc acggtcgaat cagctagacc ttcgcaacgt    720
tttcgcgctc gcacgttctt atcgatctac tgagattgac tcgaaaaagt cttctctcac    780
ggtcgattga actttgaatg aactctcagg ttgcgcgaga gccaatacga ccgaccaga    840 ggcaattcgg agcttccgg aacgttccaa ggagagggat tttccgagag attacgattg    900
cgagatagaa aaaaggctag cttcgattt cgagagagat tactttcaag ttcgctgctt    960
ccaactcttg ctccaacccc ctccactcct tctctacaaa acaccatgg              1009

<210> SEQ ID NO 56
<211> LENGTH: 2148
<212> TYPE: DNA
<213> ORGANISM: Rhodotorula glutinis ATCC 204091

<400> SEQUENCE: 56
ggcgcgccac catctcctcg tcgcttcttc cctctccttc ggcgcccaca ccgcttcgca      60
gggctcacgg actgctcaca tcgtttgtgt gcgtcgctgt gcatgtccac gcaccactcc    120
cagcccccac gagcgcctca aaagacgcgg acgcagacgc ccgccgaacg acggcacgcc    180
cctcttctca ctagcgcgac gaaccagctg cgacgattcg tgcgcttatg ttagccggac    240
ttctggcttg cttttgcgctg ctgcgtccgt cttgtggtgc ggatcggctc gatgggggtt    300
tgctcgtttg ctgggagacg gtcgcctctc cctcctcctc ttcactcctc gttagctttc    360
tacgctcatt ggttctgcga accatctaca tcacgctcgc tcgtcatgct cgtactacga    420
tcaacacccc tgctcgtcgt gctttccctc ctctccgtcc tctcggccgc gtccagcgac    480
ttgcccagcc aacttccccc gcacgccggt gagtctccca cacttccttg cgaccccaac    540
ccagcatctg acatccgcat cacgcagccc tcccgccttc ccactcctcc ctcttcaccg    600
actcctcctc ctcctcccct gattcctcgt ccctcaaagc cccgcagcct cttcccttca    660
aaatcaagcg ccccgctcg ctcgaacaag tgcagcagaa cctcgggaag aggctggcga    720

```
agcgcggcga ggaggggagt aagacggaga gggtgccgtt tggtcagagg agtgcgacgg      780
cggcgagtgc gggtggacaa ggtggagcgg gacggggag ggcgacgcag cgcgttacgg       840
gcggaggaag cagaggtgca ggaggaggcg gagggagtgt cgcggctgct cagcctgtcc      900
cttcgactac ccagacggtc gagacaggct ctaagatcgt ctcgactggt cttctgaccg      960
tagcgtcgcc gtcgacggca gatggaggag gcgggacggt cacccaggtc gagacggcct    1020
cctcaggggt attgatcacc agcacggcgg gagcggcgag ttcagcggcg cgtcggacg     1080 tcgctagcgc acaggcagcg gaggcgacgt cgagtacgag catgatcagc ggaggagcgg    1140
cggctggcgg gagtttaagc aggatgctgg cgggaggagt tgcgggtgca gccctgatcc    1200
tcctcgtgcg gtgagcaggc gaagcgagga gctcatgtag atacagcata gacagtatat    1260
atcgccagga tagcttgcaa cagccgccgg tcggtttatt ccattgtcct cgaccccatg    1320
cgaaggcgag ctctgctcgt cagctggcca agctggccag cagacgagcg ttggggtggc    1380
ggaacgccaa cggcatggag taaagcagcc gtgaggatga cggaggagct cgggcgaggt    1440 gatgggatt ctagcaggaa cagcagacg gcgaggagga gaggaaccgg aagcacagtc     1500
tcgtggccgc ttgttgcaga tcccagtgtc gctagagtgc tcgtcgtcat cagagcgagt    1560
gaacaaagcg atgccctgaa gaacgatgag cgaatgagtc gaagcggcgt ctaccggtga    1620
actcggggtg tggcaaatga gcgagacgag gagtgcccgc cagagttgcc acgtcgaccc    1680
cacgtcggaa tcgacgttga tagagtgaac gaagccattg cagacccag aaggtggcca    1740 tgttgtggaa gcgagggcag gagcgagggg agaaggcgag gaggaggagg ggctggggaa    1800
gcccgtccgg gaatggcgca gctgggtgcc ggggatgtgc gcgagtggcg gaggagtcga    1860
gcgtgagagt tctggaacac ggggcgcgca caagggtcga gggccgtgac gagttcgccg    1920
ggcggtggtc gggctgaggg cgagcgcgcg ttggggacga cgacgcccga cgccctcgct    1980
cttcgtcctc accgcttccc ggagaacttt gctgtactct gcttctccct tcacactctc    2040
acacccactc acacacccctt ccatccacac acaagctatc cgcacacctc tcacacccga    2100
ccccagctcg ccccatcctc ttcgcacccg gctcatcgaa aaccatgg                  2148
```

<210> SEQ ID NO 57
<211> LENGTH: 30
<212> TYPE: DNA
<213> ORGANISM: Artificial Sequence
<220> FEATURE:
<223> OTHER INFORMATION: oligoculeotide PCR primer

<400> SEQUENCE: 57
ggcgcgccac catctcctcg tcgcttcttc                                       30

<210> SEQ ID NO 58
<211> LENGTH: 28
<212> TYPE: DNA
<213> ORGANISM: Artificial Sequence
<220> FEATURE:
<223> OTHER INFORMATION: oligonucleotide PCR primer

<400> SEQUENCE: 58
ccatggtttt cgatgagccg ggtgcgaa                                         28